(12) United States Patent
Janzig et al.

(10) Patent No.: US 7,848,817 B2
(45) Date of Patent: Dec. 7, 2010

(54) COUPLING MODULE OF A MODULAR IMPLANTABLE MEDICAL DEVICE

(75) Inventors: Darren A. Janzig, Centerville, MN (US); Carl D. Wahlstrand, Lino Lakes, MN (US); Robert M. Skime, Coon Rapids, MN (US); Mark S. Lent, Brooklyn Park, MN (US); Keith A. Miesel, St. Paul, MN (US); James E. Cabak, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1551 days.

(21) Appl. No.: 10/731,699

(22) Filed: Dec. 9, 2003

(65) Prior Publication Data

US 2004/0172090 A1  Sep. 2, 2004

Related U.S. Application Data

(60) Provisional application No. 60/431,854, filed on Dec. 9, 2002, provisional application No. 60/471,262, filed on May 16, 2003, provisional application No. 60/503,945, filed on Sep. 20, 2003, provisional application No. 60/503,946, filed on Sep. 20, 2003, provisional application No. 60/507,857, filed on Oct. 1, 2003.

(51) Int. Cl.
*A61N 1/00* (2006.01)

(52) U.S. Cl. ........................................ 607/45

(58) Field of Classification Search ............... 607/45, 607/28, 4, 21, 36, 61, 122, 129, 2, 5; 623/11, 623/11.11; 455/90.3
See application file for complete search history.

(56) References Cited

U.S. PATENT DOCUMENTS

| | | | |
|---|---|---|---|
| 3,690,325 A | 9/1972 | Kenny | |
| 3,720,874 A * | 3/1973 | Gorcik et al. | 455/90.3 |
| 3,724,467 A | 4/1973 | Avery et al. | |
| 3,888,260 A | 6/1975 | Fischell | |
| 3,913,587 A | 10/1975 | Newash | |
| 3,941,135 A | 3/1976 | von Sturm et al. | |
| 4,006,748 A | 2/1977 | Schulman | |
| 4,013,081 A | 3/1977 | Kolenik | |
| 4,040,412 A | 8/1977 | Sato | |
| 4,094,321 A | 6/1978 | Muto | |

(Continued)

FOREIGN PATENT DOCUMENTS

| | | |
|---|---|---|
| DE | 3940632 | 12/1990 |
| GB | 1 161 579 | 8/1969 |
| WO | WO 92/20402 | 11/1992 |
| WO | WO 00/13743 | 3/2000 |
| WO | WO 00/40295 | 7/2000 |

(Continued)

OTHER PUBLICATIONS

U.S. Appl. No. 10/731,868, filed Dec. 9, 2003, entitled "Implantation of Low-Profile Implantable Medical Device".
U.S. Appl. No. 10/730,873, filed Dec. 9, 2003, entitled "Overmold for a Modular Implantable Medical Device".
U.S. Appl. No. 10/731,881, filed Dec. 9, 2003, entitled "Reducing Relative Intermodule Motion in a Modular Implantable Medical Device".

(Continued)

*Primary Examiner*—George Manuel
(74) *Attorney, Agent, or Firm*—Shumaker & Sieffert, P.A.

(57) ABSTRACT

In an implantable medical device having individual modules, a coupling module couples the modules to one another. The coupling module supports electrical and/or mechanical coupling of the modules. The coupling module may assume a variety of shapes or configurations. The various embodiments of the coupling module may offer the modules varying degrees of freedom of movement relative to one another.

26 Claims, 18 Drawing Sheets

U.S. PATENT DOCUMENTS

| | | | |
|---|---|---|---|
| 4,256,115 A | 3/1981 | Bilitch | |
| 4,266,552 A | 5/1981 | Dutcher et al. | |
| 4,328,813 A | 5/1982 | Ray | |
| 4,399,819 A | 8/1983 | Cowdery | |
| 4,399,820 A * | 8/1983 | Wirtzfeld et al. | 607/21 |
| 4,499,907 A * | 2/1985 | Kallok et al. | 607/122 |
| 4,616,655 A | 10/1986 | Weinberg et al. | |
| 4,911,178 A | 3/1990 | Neal | |
| 4,928,696 A | 5/1990 | Henderson et al. | |
| 4,934,368 A * | 6/1990 | Lynch | 607/2 |
| 4,969,899 A | 11/1990 | Cox | |
| 4,972,846 A * | 11/1990 | Owens et al. | 607/129 |
| 5,085,644 A | 2/1992 | Watson et al. | |
| 5,116,345 A | 5/1992 | Jewell et al. | |
| 5,144,946 A | 9/1992 | Weinberg et al. | |
| 5,197,332 A | 3/1993 | Shennib | |
| 5,207,218 A | 5/1993 | Carpentier et al. | |
| 5,218,959 A | 6/1993 | Fenster | |
| 5,220,929 A | 6/1993 | Marquit | |
| 5,252,090 A | 10/1993 | Giurtino et al. | |
| 5,271,397 A | 12/1993 | Seligman et al. | |
| 5,312,440 A * | 5/1994 | Hirschberg et al. | 607/5 |
| 5,314,451 A | 5/1994 | Mulier | |
| 5,314,453 A | 5/1994 | Jeutter | |
| 5,411,538 A | 5/1995 | Lin | |
| H1465 H | 7/1995 | Stokes | |
| 5,431,695 A | 7/1995 | Wiklund et al. | |
| 5,433,734 A | 7/1995 | Stokes et al. | |
| 5,455,999 A | 10/1995 | Weiss et al. | |
| 5,458,997 A | 10/1995 | Crespi et al. | |
| 5,480,416 A | 1/1996 | Garcia et al. | |
| 5,489,225 A | 2/1996 | Julian | |
| 5,554,194 A | 9/1996 | Sanders | |
| 5,562,715 A | 10/1996 | Czura et al. | |
| 5,571,148 A | 11/1996 | Loeb et al. | |
| 5,573,551 A | 11/1996 | Lin et al. | |
| 5,613,935 A | 3/1997 | Jarvik | |
| 5,645,586 A * | 7/1997 | Meltzer | 623/11.11 |
| 5,674,260 A | 10/1997 | Weinberg | |
| 5,678,559 A | 10/1997 | Drakulic | |
| 5,702,430 A | 12/1997 | Larson, Jr. et al. | |
| 5,741,313 A | 4/1998 | Davis et al. | |
| 5,755,743 A | 5/1998 | Volz et al. | |
| 5,776,169 A * | 7/1998 | Schroeppel | 607/36 |
| 5,792,067 A | 8/1998 | Karell | |
| 5,800,535 A | 9/1998 | Howard, III | |
| 5,814,095 A | 9/1998 | Müller et al. | |
| 5,843,150 A | 12/1998 | Dreessen et al. | |
| 5,873,899 A | 2/1999 | Stutz, Jr. et al. | |
| RE36,120 E | 3/1999 | Karell | |
| 5,876,424 A | 3/1999 | O'Phelan et al. | |
| 5,895,414 A | 4/1999 | Sanchez-Zambrano | |
| 5,896,647 A | 4/1999 | Shkuratoff | |
| 5,919,215 A | 7/1999 | Wiklund et al. | |
| 5,935,154 A | 8/1999 | Westlund | |
| 5,941,905 A | 8/1999 | Single | |
| 5,941,906 A | 8/1999 | Barreras, Sr. et al. | |
| 5,954,751 A | 9/1999 | Chen et al. | |
| 5,954,757 A | 9/1999 | Gray | |
| 5,958,088 A | 9/1999 | Vu et al. | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,016,593 A | 1/2000 | Kyrstein | |
| 6,044,304 A | 3/2000 | Baudino | |
| 6,061,593 A | 5/2000 | Fischell et al. | |
| 6,067,474 A | 5/2000 | Schulman et al. | |
| 6,091,979 A | 7/2000 | Madsen | |
| 6,112,120 A | 8/2000 | Correas | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,162,487 A | 12/2000 | Darouiche | |
| 6,168,580 B1 | 1/2001 | Yardley | |
| 6,176,879 B1 * | 1/2001 | Reischl et al. | 623/11.11 |
| 6,205,358 B1 | 3/2001 | Haeg et al. | |
| 6,214,032 B1 | 4/2001 | Loeb et al. | |
| 6,218,016 B1 | 4/2001 | Tedeschi et al. | |
| 6,230,049 B1 | 5/2001 | Fischell et al. | |
| 6,248,080 B1 | 6/2001 | Miesel et al. | |
| 6,259,951 B1 | 7/2001 | Kuzma et al. | |
| 6,263,225 B1 | 7/2001 | Howard, III | |
| 6,266,556 B1 | 7/2001 | Ives et al. | |
| 6,269,266 B1 | 7/2001 | Leysieffer | |
| 6,272,382 B1 | 8/2001 | Faltys et al. | |
| 6,308,101 B1 | 10/2001 | Faltys et al. | |
| 6,324,428 B1 | 11/2001 | Weinberg et al. | |
| 6,330,468 B1 | 12/2001 | Scharf | |
| 6,354,299 B1 | 3/2002 | Fischell et al. | |
| 6,356,792 B1 | 3/2002 | Zonenshayn et al. | |
| 6,358,281 B1 | 3/2002 | Berrang et al. | |
| 6,360,122 B1 | 3/2002 | Fischell et al. | |
| 6,366,813 B1 | 4/2002 | DiLorenzo | |
| 6,405,079 B1 | 6/2002 | Ansarinia | |
| 6,415,184 B1 | 7/2002 | Ishikawa et al. | |
| 6,427,086 B1 | 7/2002 | Fischell et al. | |
| 6,436,422 B1 | 8/2002 | Trogolo et al. | |
| 6,445,956 B1 | 9/2002 | Laird et al. | |
| 6,456,256 B1 | 9/2002 | Amundson et al. | |
| 6,456,886 B1 | 9/2002 | Howard, III et al. | |
| 6,480,743 B1 | 11/2002 | Kirkpatrick et al. | |
| 6,490,486 B1 * | 12/2002 | Bradley | 607/28 |
| 6,498,951 B1 | 12/2002 | Larson et al. | |
| 6,505,077 B1 | 1/2003 | Kast et al. | |
| 6,516,227 B1 | 2/2003 | Meadows et al. | |
| 6,516,808 B2 | 2/2003 | Schulman | |
| 6,517,476 B1 | 2/2003 | Bedoya et al. | |
| 6,537,200 B2 | 3/2003 | Leysieffer et al. | |
| 6,554,762 B2 | 4/2003 | Leysieffer | |
| 6,560,486 B1 | 5/2003 | Osorio et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 | 7/2003 | Pless et al. | |
| 6,618,623 B1 | 9/2003 | Pless et al. | |
| 6,626,680 B2 | 9/2003 | Ciurzynski et al. | |
| 6,648,914 B2 | 11/2003 | Berrang et al. | |
| 6,671,544 B2 | 12/2003 | Baudino | |
| 6,726,678 B1 | 4/2004 | Nelson et al. | |
| 6,788,974 B2 | 9/2004 | Bardy et al. | |
| 6,805,998 B2 | 10/2004 | Jenson et al. | |
| 6,882,881 B1 | 4/2005 | Lesser et al. | |
| 6,899,976 B2 | 5/2005 | Larson et al. | |
| 6,963,780 B2 | 11/2005 | Ruben et al. | |
| 6,994,933 B1 | 2/2006 | Bates | |
| 7,010,351 B2 | 3/2006 | Firlik et al. | |
| 7,063,691 B2 | 6/2006 | Nelson et al. | |
| 7,103,415 B2 | 9/2006 | Probst et al. | |
| 7,107,097 B2 | 9/2006 | Stern et al. | |
| 7,110,819 B1 | 9/2006 | O'Hara | |
| 7,212,864 B2 | 5/2007 | Wahlstrand et al. | |
| 7,242,982 B2 | 7/2007 | Singhal et al. | |
| 7,263,401 B2 | 8/2007 | Scott et al. | |
| 7,454,251 B2 | 11/2008 | Rezai et al. | |
| 2001/0033953 A1 | 10/2001 | Gan et al. | |
| 2001/0051819 A1 | 12/2001 | Fischell et al. | |
| 2002/0002390 A1 | 1/2002 | Fischell et al. | |
| 2002/0013612 A1 | 1/2002 | Whitehurst | |
| 2002/0019669 A1 | 2/2002 | Berrang et al. | |
| 2002/0037756 A1 | 3/2002 | Jacobs et al. | |
| 2002/0042634 A1 | 4/2002 | Bardy et al. | |
| 2002/0051550 A1 | 5/2002 | Leysieffer | |
| 2002/0068958 A1 | 6/2002 | Bardy et al. |

| | | | |
|---|---|---|---|
| 2002/0087201 A1 | 7/2002 | Firlik et al. | |
| 2002/0099412 A1 | 7/2002 | Fischell et al. | |
| 2002/0103510 A1 | 8/2002 | Bardy et al. | |
| 2002/0107546 A1 | 8/2002 | Ostroff et al. | |
| 2002/0165588 A1 | 11/2002 | Fraley et al. | |
| 2002/0169485 A1 | 11/2002 | Pless et al. | |
| 2002/0177882 A1 | 11/2002 | DiLorenzo | |
| 2003/0004428 A1 | 1/2003 | Pless et al. | |
| 2003/0004546 A1 | 1/2003 | Casey | |
| 2003/0017372 A1 | 1/2003 | Probst et al. | |
| 2003/0040781 A1 | 2/2003 | Larson et al. | |
| 2003/0073972 A1 | 4/2003 | Rosenman et al. | |
| 2003/0085684 A1 | 5/2003 | Tsukamoto et al. | |
| 2003/0088294 A1 | 5/2003 | Gesotti | |
| 2003/0091893 A1 | 5/2003 | Kishiyama et al. | |
| 2003/0109903 A1 | 6/2003 | Berrang et al. | |
| 2003/0120320 A1 | 6/2003 | Solom | |
| 2003/0125786 A1 | 7/2003 | Gliner et al. | |
| 2003/0130706 A1 | 7/2003 | Sheffield et al. | |
| 2003/0171787 A1 | 9/2003 | Money et al. | |
| 2003/0204229 A1 | 10/2003 | Stokes | |
| 2004/0082977 A1 | 4/2004 | Engmark et al. | |
| 2004/0102828 A1 | 5/2004 | Lowry et al. | |
| 2004/0176815 A1 | 9/2004 | Janzig et al. | |
| 2004/0181263 A1 | 9/2004 | Balzer et al. | |
| 2004/0186528 A1 | 9/2004 | Ries et al. | |
| 2005/0004620 A1 | 1/2005 | Singhal et al. | |
| 2005/0033378 A1 | 2/2005 | Sheffield et al. | |
| 2005/0070971 A1 | 3/2005 | Fowler et al. | |
| 2005/0075679 A1 | 4/2005 | Gliner et al. | |
| 2006/0116743 A1 | 6/2006 | Gibson et al. | |
| 2006/0129205 A1 | 6/2006 | Boveja et al. | |
| 2006/0149336 A1 | 7/2006 | Meadows | |
| 2006/0184210 A1 | 8/2006 | Singhal et al. | |
| 2006/0195156 A1 | 8/2006 | Singhal et al. | |
| 2006/0253106 A1 | 11/2006 | Nelson et al. | |
| 2007/0074732 A1 | 4/2007 | Singhal et al. | |
| 2007/0185539 A1 | 8/2007 | Singhal et al. | |
| 2007/0255338 A1 | 11/2007 | Wahlstrand | |
| 2008/0021511 A1 | 1/2008 | Wahlstrand et al. | |
| 2008/0065173 A1 | 3/2008 | Wahlstrand et al. | |
| 2009/0292327 A1 | 11/2009 | Singhal et al. | |
| 2009/0299164 A1 | 12/2009 | Singhal et al. | |
| 2009/0299165 A1 | 12/2009 | Singhal et al. | |
| 2009/0299380 A1 | 12/2009 | Singhal et al. | |
| 2010/0114249 A1 | 5/2010 | Wahlstrand et al. | |

FOREIGN PATENT DOCUMENTS

| | | |
|---|---|---|
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |
| WO | WO 2004/052458 | 6/2004 |

OTHER PUBLICATIONS

U.S. Appl. No. 10/730,878, filed Dec. 9, 2003, entitled "Lead Interconnect Module of a Modular Implantable Medical Device".

U.S. Appl. No. 10/730,877, filed Dec. 9, 2003, entitled "Low-Profile Implantable Medical Device".

U.S. Appl. No. 10/731,867, filed Dec. 9, 2003, entitled "Concavity of an Implantable Medical Device".

U.S. Appl. No. 10/731,638, filed Dec. 9, 2003, entitled "Modular Implantable Medical Device".

U.S. Appl. No. 10/731,869, filed Dec. 9, 2003, entitled "Modular Implantable Medical Device".

"Surgical Process," Animation Screenshots from http://www.cochlearamerica.com/800.asp, 7 pgs.

"Candidates Brochure," http://www.cochlearamerica.com/pdfs/candidatebrochglobal.pdf, 14 pgs.

"Research and Development," http://www.cochlearamericas.com/384.asp, 1 pg.

"The World Leader in cochlear implants—revolutionizing hearing for adults and infants," http://www.cochlear.com, 1 pg.

"Cochlear: innovator of the Nucleus 3 cochlear implant system," http://www.cochlearamericas.com, 1 pg.

"What is a Cochlear Implant," http://www.cochlearamericas.com/What/161.asp, 1 pg.

"ESPrit 3G Speech Processor," http://www.cochlearamericas.com/591.asp, 2 pgs.

"Nucleus 3 System," http://www.cochlearamericas.com/Products/465.asp, 1 pg.

"Internal Components: Nucleus 24 Cochlear Implants," http://www.cochlearamericas.com/374.asp, 1 pg.

"Nucleus 24 Contour," http://www.cochlearamericas.com/568.asp, 2 pgs.

"Nucleus 24 M," http://www.cochlearamericas.com/372.asp, 1 pg.

"Nucleus 24 K," http://www.cochlearamericas.com/371.asp, 1 pg.

"Nucleus 24 Double Array," http://www.cochlearamericas.com/370.asp, 1 pg.

"Nucleus 24 ABI: Auditory Brainstem Implant," http://www.cochlearamericas.com/373.asp, 2 pgs.

"Nucleus Speech Processors," http://www.cochlearamericas.com/629.asp, 1 pg.

"Sprint: body worn speech processor," http://www.cochlearamericas.com/1010.asp, 1 pg.

"Cochlear," http://www.cochlearamericas.com/Recipients/978.asp, 3 pgs.

Answers.com, www.answers.com, defined: discrete components, acessed on Mar. 2, 2007 (2 pages).

Notification of Transmittal of the International Search Report dated May 7, 2004, International Application No. PCT/US03/38938.

Written Opinion dated Dec. 16, 2004, International Application No. PCT/US03/38938.

Notification of Transmittal of the International Preliminary Examination Report dated Apr. 11, 2005, International Application No. PCT/US03/38938.

U.S. Appl. No. 10/837,319, filed Apr. 30, 2004, entitled "Implantable Medical Device With Anti-Infection Agent."

U.S. Appl. No. 10/835,527, filed Apr. 29, 2004, entitled "Implantation of Implantable Medical Device."

U.S. Appl. No. 10/835,232, filed Apr. 29, 2004, entitled "Explanation of Implantable Medical Device."

U.S. Appl. No. 10/835,233, filed Apr. 29, 2004, entitled "Implantable Medical Device With A Nonhermetic Battery."

U.S. Appl. No. 10/835,548, filed Apr. 29, 2004, entitled "Headset Recharger For Cranially Implantable Medical Devices."

U.S. Appl. No. 10/835,245, filed Apr. 29, 2004, entitled "Battery Housing Configuration."

U.S. Appl. No. 10/837,276, filed Apr. 30, 2004, entitled "Implantable Medical Device With Lubricious Material."

European Communication from corresponding European Application No. 03 790 404.2-2305 mailed Jun. 19, 2009 (3 pages).

* cited by examiner

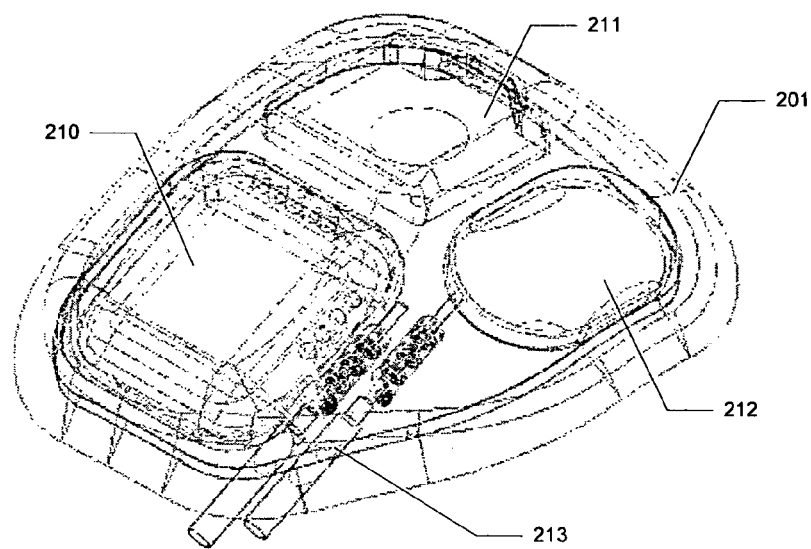
FIG. 2
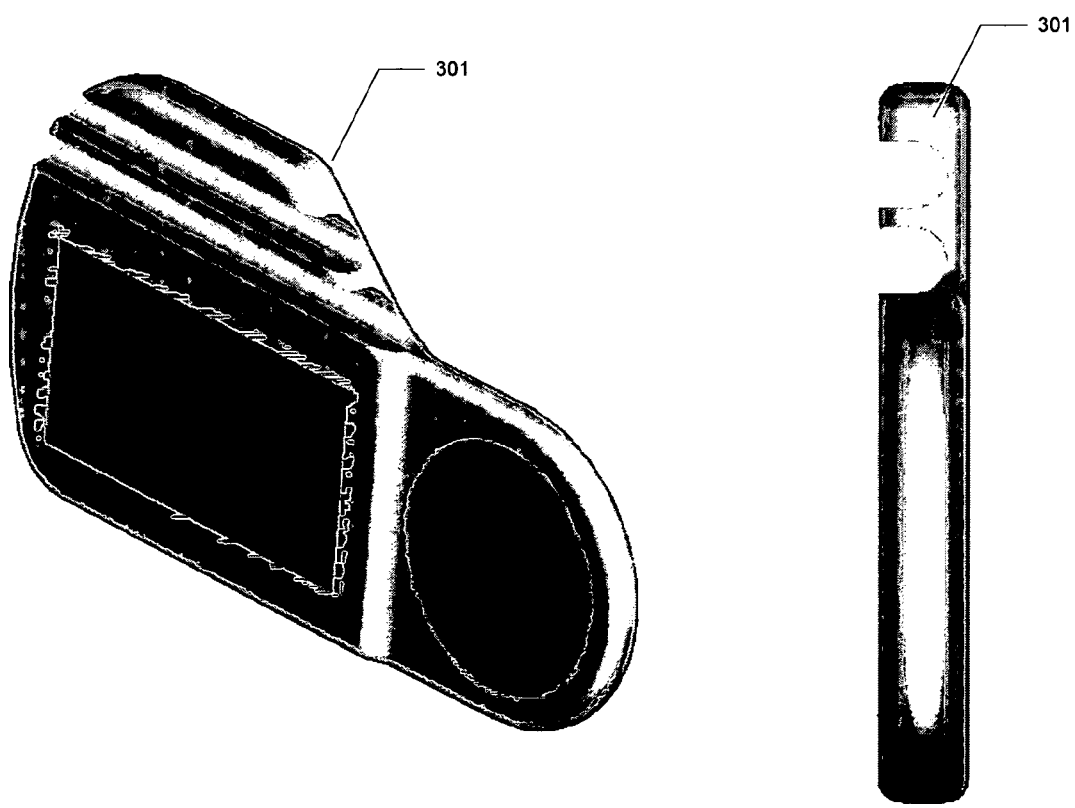
FIG. 3A
FIG. 3B

Side View

COUPLING MODULE OF A MODULAR IMPLANTABLE MEDICAL DEVICE

This application claims the benefit of:

1. U.S. Provisional Application entitled "CRANIAL NEUROSTIMULATOR AND METHOD," Ser. No. 60/431,854, filed on Dec. 9, 2002;

2. U.S. Provisional Application entitled "Implantable Cranial Medical Devices and Methods," Ser. No. 60/471,262, filed on May 16, 2003;

3. U.S. Provisional Application entitled "IMPLANTABLE CRANIAL MEDICAL DEVICES AND METHODS," Ser. No. 60/503,945, filed on Sep. 20, 2003;

4. U.S. Provisional Application entitled "IMPLANTABLE CRANIAL MEDICAL DEVICES AND METHODS," Ser. No. 60/503,946, filed on Sep. 20, 2003; and 5. U.S. Provisional Application entitled "Thin Neuro Stimulation System, Device and Method," Ser. No. 60/507,857, filed on Oct. 1, 2003. The entire content of each of these U.S. Provisional Applications is incorporated herein by reference.

The following co-pending and commonly-assigned U.S. Patent Applications, filed on even date herewith, are also incorporated herein by reference in their entirety:

1. U.S. Patent Application entitled "MODULAR IMPLANTABLE MEDICAL DEVICE," to Carl D. Wahlstrand et al., filed Dec. 9, 2003, assigned U.S. application Ser. No. 10/731,638;

2. U.S. Patent Application entitled "IMPLANTATION OF LOW-PROFILE IMPLANTABLE MEDICAL DEVICE," to Ruchika Singhal et al., filed Dec. 9, 2003, assigned U.S. application Ser. No. 10/731,868;

3. U.S. Patent Application entitled "OVERMOLD FOR A MODULAR IMPLANTABLE MEDICAL DEVICE," to Ruchika Singhal et al., filed Dec. 9, 2003, U.S. application Ser. No. 10/730,873;

4. U.S. Patent Application entitled "REDUCING RELATIVE INTER-MODULE MOTION IN A DISTRIBUTED MODULAR IMPLANTABLE MEDICAL DEVICE," to Carl D. Wahlstrand et al., filed Dec. 9, 2003, assigned U.S. application Ser. No. 10/731,881;

5. U.S. Patent Application entitled "LEAD CONNECTION MODULE OF A MODULAR IMPLANTABLE MEDICAL DEVICE," to Ruchika Singhal et al., filed Dec. 9, 2003, assigned U.S. application Ser. No. 10/730,878;

6. U.S. Patent Application entitled "LOW-PROFILE IMPLANTABLE MEDICAL DEVICE," to Darren A. Janzig et al., filed Dec. 9, 2003, assigned U.S. application Ser. No. 10/730,877; and 7. U.S. Patent Application entitled "CONCAVITY OF AN IMPLANTABLE MEDICAL DEVICE," to Carl D. Wahlstrand et al., filed Dec. 9, 2003, assigned U.S. application Ser. No. 10/731,867.

8. U.S. Patent Application entitled "MODULAR IMPLANTABLE MEDICAL DEVICE," to Carl D. Wahlstrand et al., filed Dec. 9, 2003, assigned U.S. application Ser. No. 10/731.869.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from titanium because of its desirable rigidity and biocompatibility.

The size and shape of an IMD housing is dependant on the sizes and shapes of the components of the IMD. Large components common to most IMDs include a battery, a telemetry coil, and a hybrid circuit that includes digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention relates to a coupling module for a modular implantable medical device. In order to provide an implantable medical device with a smaller profile so that the IMD can better fit into available body locations, various functional components of the IMD are separated into individual interconnected modules. This modular architecture for the implantable medical device permits the device footprint to be distributed over a larger area while making the profile smaller.

The multiple modules and their respective flexible interconnections are typically coupled to one another mechanically and electrically. Electrical coupling permits the modules to receive power or signals from one another, for example. Mechanical coupling helps constrain the modules while also providing some freedom of movement. In general, it is desirable that a modular IMD include some freedom of movement, so that the IMD may conform to the body location into which it is to be implanted. The present invention is directed to one or more coupling mechanisms for the modular component modules within the implantable medical device. The coupling mechanisms support mechanical and electrical coupling of the modules.

In one embodiment, the invention is directed to an implantable medical device that includes at least two modules, each of the modules comprising a housing. The IMD also includes a coupling module coupled to each of the modules. The coupling module defines at least one lumen between the modules and permits motion of the two modules along at least one axis of motion.

In another embodiment, the invention presents a device comprising a first module that includes control electronics comprising a first housing, a second module comprising a second housing, and a coupling module fixedly coupled to the first and second housings. The coupling module defines at least one lumen and permits motion of the first housing relative to the second housing and along at least one axis of motion. The coupling module may assume a variety of configurations. The coupling module may include, for example, multiple lumens, a shaped cross-section or a helical portion.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 2 is a schematic diagram illustrating an implantable medical device according to another embodiment of the present invention.

FIGS. 3A and 3B are schematic diagrams illustrating an implantable medical device according to another embodiment of the present invention.

FIGS. 10A-10I are schematic diagrams illustrating exemplary shapes, configurations and features of a coupling module according to embodiments of the present invention.

DETAILED DESCRIPTION

Figure 1A:
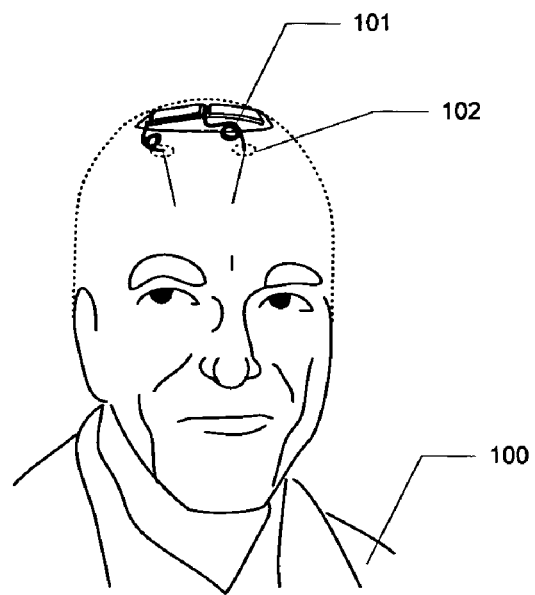
FIGS. 1A and 1B are diagrams illustrating use of an implantable medical device in a patient according to an example embodiment of the present invention.
Figure 1B:
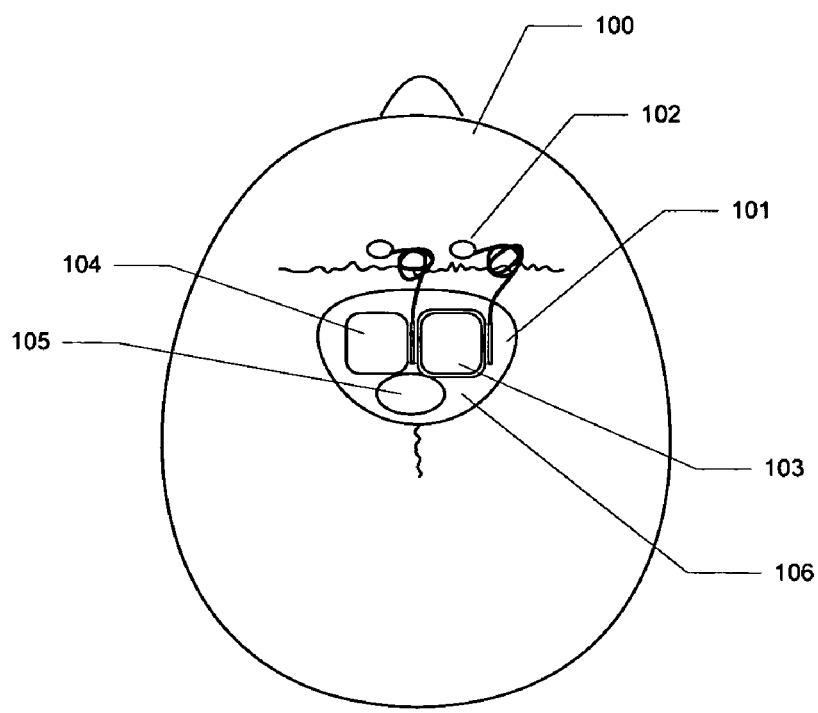

FIGS. 1A and 1B are diagrams illustrating use of an implantable medical device (IMD) in a patient according to an example embodiment of the present invention. An IMD101 is implanted within a patient 100 in order to permit IMD101 to provide therapies to the patient 100. In the example illustrated within FIGS. 1A-1B, IMD101 is implanted under the scalp of the patient 100 in order to locate the device 101 as close as possible to the location of leads 102 that provide the therapy.

FIG. 1A shows patient 100 with IMD 101 deployed beneath his scalp. In FIG. 1A, IMD 101 is a neurostimulator that provides deep brain stimulation via leads 102 deployed in the brain of patient 100. IMD 101 is deployed in proximity to site of stimulation therapy. IMD 101 may be used to treat any nervous system disorder including, but not limited to, epilepsy, pain, psychological disorders including mood and anxiety disorders, movement disorders (MVD) such as, but not limited to, essential tremor and Parkinson's disease and neurodegenerative disorders.

Although IMD 101 is depicted as a neurostimulator, the invention is not limited to applications in which the IMD is a neurostimulator. The invention may be employed with IMDs that perform any monitoring or therapeutic functions. The invention is not limited to IMDs that include leads deployed in the brain, but may also be employed with leads deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Nor is the invention limited to IMDs that are coupled to electrodes. The invention may be employed with IMDs coupled to any sensing or therapeutic elements, such as temperature sensors or motion sensors. The invention may also be employed with different types of IMDs including, but not limited to, IMDs operating in an open loop mode (also referred to as nonresponsive operation), IMDs operating in a closed loop mode (also referred to as responsive), and IMDs for providing monitoring and/or warning.

In general, IMD 101 has a low profile, i.e., IMD 101 is thin to permit IMD 101 to be deployed effectively, comfortably and cosmetically and under the scalp. In one embodiment of the invention, IMD 101 has a maximum thickness of between approximately 4 millimeters and approximately 8 millimeters. The use of a reduced profile may reduce the risk of infection, skin erosion and cosmetic issued related to the implantation of IMD 101.

Many locations within a patient do not present adequate profile for implantable medical devices. As such, many uses of such devices employ lengthy leads located remote from an implantation site of the IMD. The use of these lengthy leads requires complicated insertion procedures from the site of the IMD to the site of lead deployment that may cause medical complications to the patient as well as may lead to failures in connection leads. By constructing IMD 101 as a set of distributed modules connected together as described herein, IMD 101 may be deployed proximate to a treatment or monitoring site.

While the embodiment of IMD 101 shown in FIGS. 1A-1B is implanted under the scalp of patient 100 and may be used when the therapy provided to patient 100 includes neural stimulation of a brain, other embodiments of IMD 100 permit the device to be implanted at many other locations within the body. In addition, IMD 101 includes a plurality of interconnected modules. Each module generally perform assigned functions.

In the typical embodiment depicted in FIG. 1B, IMD 101 includes three modules, namely, a control module 103, a power supply module 104 and a recharge module 105. Control module 103 typically includes the electronic components associated with the functions of IMD 101. In a typical implementation, control module 103 may include a hybrid circuit that includes digital circuits such as integrated circuit chips and one or more microprocessors, and analog circuit components. Accordingly, control module 103 may also be referred to as an electronic module. Power supply module 104 typically comprises one or more energy storage devices, such as a rechargeable lithium ion battery. Recharge module 105 typically includes one or more coils for transmitting or receiving electromagnetic energy through the scalp. The transmitted energy may include energy to be stored in power supply module 104. In some embodiments, the transmitted energy may also include communication, such as information encoded in radio frequency transmissions.

Individual modules 103 and 104 may be encased in biocompatible metal shields such as titanium shield halves, and may be sealed against contamination. In addition, individual modules 103 and 104 may include insulation to electrically isolate the electrical components inside the modules from the metal shields. The modules are coupled to an overmold 106 which may be made of a biocompatible material. Use of the term "overmold" herein is not intend to limit the invention to embodiments in which the overmold is a molded structure. Overmold may be a molded structure, or may be a structure formed by any process. In addition, one or more coupling modules (not shown in FIG. 1A) may couple one or more modules to one another.

In some embodiments of the invention, overmold 106 encases all modules 103, 104 and 105. In other embodiments, overmold 106 is disposed over or around the modules without encasing the modules. In further embodiments, overmold 106 acts as a "frame" to hold the modules in a fixed position relative to one another, but does not fully cover the modules.

Some features of the overmold, and variations on the shape of the overmold, are presented below. In general, the shape of the overmold depends upon the arrangement of the modules. The overmold may be made of a variety of materials, such as flexible silicone. The overmold may also include a rigid polymer such as Ticothane surrounded by flexible silicone. The invention is not limited to these materials, however, and the overmold may comprise any combination of elastomeric and/or non-elastomeric materials.

FIG. 2 is a schematic diagram illustrating an IMD 201 according to another embodiment of the present invention. In this example embodiment, IMD 201 is arranged in a triangular configuration. IMD 201 includes three separate modules: a control module 210, a power source module 211, and a recharge module 212. These three modules are connected together to construct IMD 201. IMD 201 also contains a set of lead connection elements 213 that permit external leads to be connected to the control module 210 as needed. The triangular configuration of IMD 201 permit IMD 201 to possess a thin profile by spreading the modules over a larger surface area. In order to minimize the surface area compact, a triangular configuration is used. The configuration of IMD 201 may also be manipulated to conform to the shape of the location within a patient in which the device is being implanted. For example, implantation of IMD 201 under the scalp of a patient may be accomplished if the overall shape of IMD 201 is curved to follow the shape of a patient's skull. Any number of shapes may be used to match a particular IMD 201 to an implantation location for a device.

FIGS. 3A and 3B are schematic diagrams illustrating an IMD 301 according to another embodiment of the present invention. In this embodiment of IMD 301, a flat device is shown that consists of multiple modules. This embodiment may be used in other locations within a patient in which the implantation location does not require such an exact match between the device and physical structures of the patient such as bone or muscle. IMD 301 may still be a modular device consisting of multiple modules as IMD 301 may provide a smaller profile when implanted as to not protrude excessively once implanted. IMD 301 need not be rigid, and in some embodiments the orientation of the modules of IMD 310 may change relative to one another.

The flat embodiment shown in FIGS. 3A-3B may represent a device that may be a pectoral implant that may be used to treat angina, to provide vagal nerve stimulation, or to provide cardiac rhythm management. Similar devices may be implanted into an upper buttock implant location, into an abdomen location, and into periphery. A device implanted into an upper buttock location may be useful in a configuration for urological and gastrological implantation therapies. A device implanted into an abdomen location may be useful a configuration for providing pain, spasticity, and chemotherapy treatment. A device implanted into a periphery location may be useful a configuration for providing muscle stimulation, on-site nerve stimulation, and diaphragm stimulation therapies. These devices may both provide therapies as well as provide a platform for sensing conditions present within a patient.

Additional alternate embodiments for implantable medical devices implemented according to principles of the present invention may also include non-electrical based therapies such as targeted introduction of fluids and similar therapeutic agents using pumps and reservoirs. One skilled in the art will recognize that any number of implantable devices may be possible without deviating from the spirit and scope of the present invention as recited within the attached claims.

FIGS. 4A-4F are schematic diagrams illustrating exemplary configurations and orientations of modules within IMD 401A through 401F (hereinafter 410), according to various embodiments of the present invention. IMD 401 consists of multiple modules that may be arranged into any number of orientations as shown in the various embodiments of FIGS. 4A-4F. For reference, each IMD 401 is depicted deployed proximate to the skull of a patient, with leads 402A and 402B deployed through burr holes 403A and 403B and coupled to IMD 401. The leads are coupled to the IMD via lead connection modules 415A and 415B. As shown in FIGS. 4A-4F, the lead connection modules may assume a variety of orientations relative to other components of IMD 401.

Figure 4A:
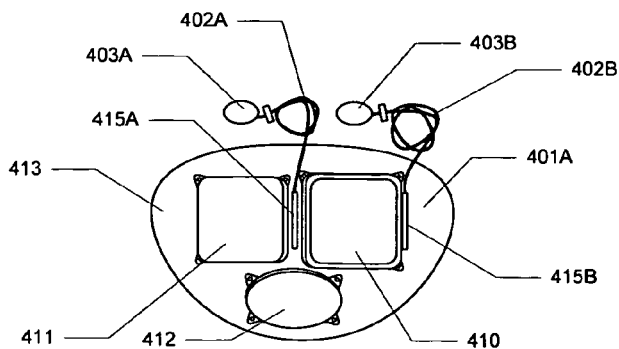
FIGS. 4A-4F are schematic diagrams illustrating various orientations of multiple modules within an implantable medical device according to various embodiments of the present invention.
Figure 4B:
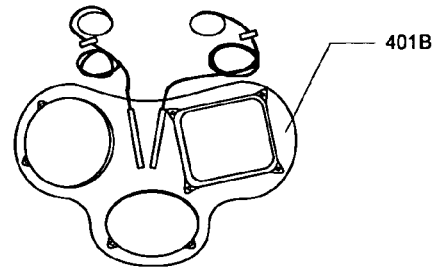
Figure 4C:
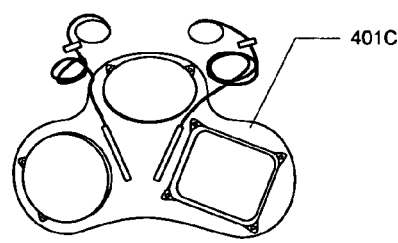
Figure 4D:
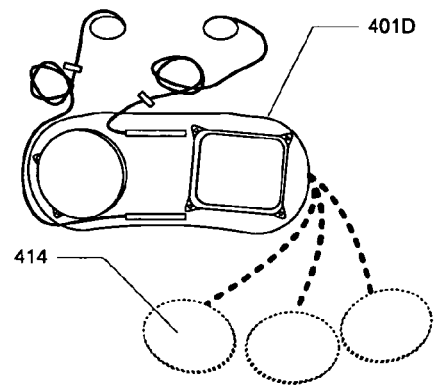
Figure 4E:
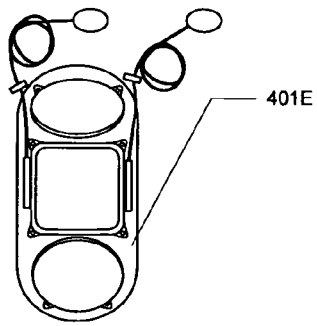
Figure 4F:
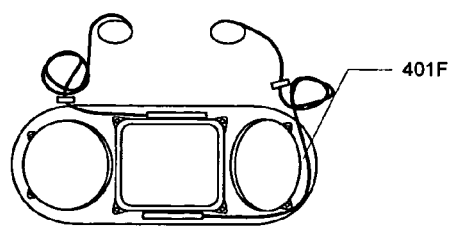

In each of these embodiments, IMD 401 has three modules as discussed above in reference to FIGS. 1B and 2: a control module 410, a power source module 411, and a recharge module 412. An overmold 413 at least partially covers the housings of control module 410 and power source module 411. The modules may be arranged into a number of orientations as long as any interconnections between the modules may be routed within the device. The various embodiments include triangular configurations, as is shown in FIGS. 4A-4C, or linear configurations as shown in FIGS. 4D-4F. In FIG. 4D, one of the three modules, such as the recharge module, is deployed as a tethered module 414 rather than being covered by overmold 413.

The invention is not limited to the deployments of the lead connection modules shown in FIGS. 4A-4F. The lead connection modules may be located on various positions within IMD 401. Lead connection modules may be oriented, for example, to permit the leads to be routed to lead locations in an efficient manner or to support management of excess lead length. Any number of other orientations and alternate embodiments may be constructed according to principles of the present invention and consistent with the claims recited herein.

In each of the exemplary embodiments depicted in FIGS. 4A-4F, any two modules may be interconnected via one or more coupling modules (not shown in FIGS. 4A-4F). The particular coupling modules may depend upon the number of modules, the distance of the modules from one another, the amount of motion or displacement of one module from another, the expected direction or directions of displacement, whether the modules are arranged in a triangular, linear or other configuration, and so on.

Figure 5A:
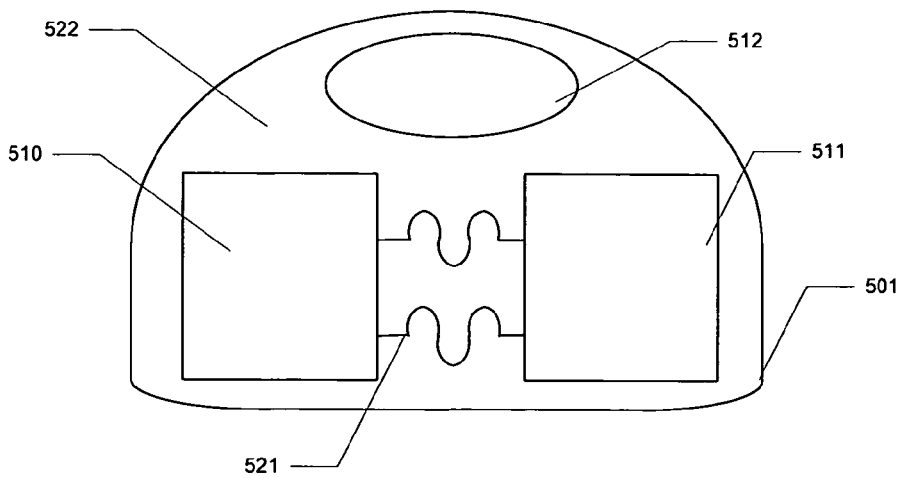
FIG. 5A is a schematic diagram illustrating the construction of an overmold and modules used in construction of an implantable medical device according to the present invention.
Figure 5B:
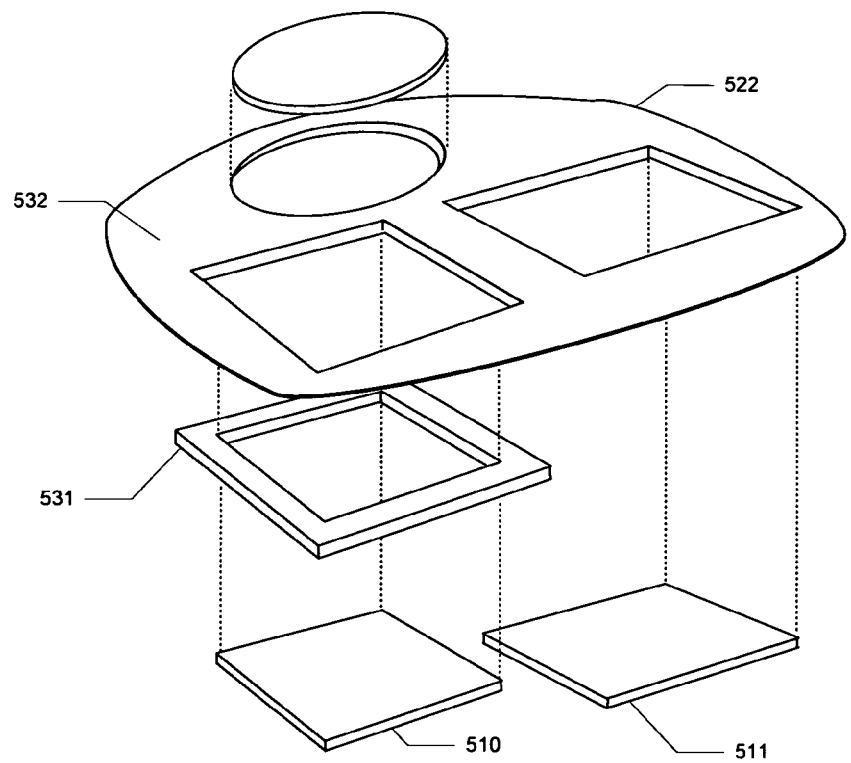
FIG. 5B is an exploded view of an embodiment of the overmold and modules shown in FIG. 5A.
Figure 5C:
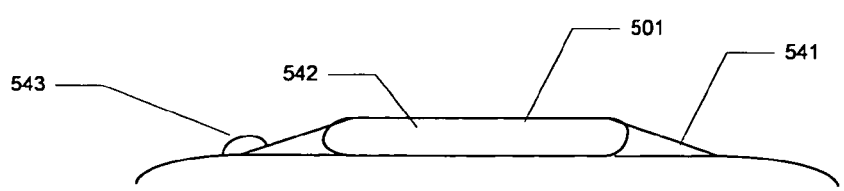
FIG. 5C is a side view of an embodiment of the overmold and modules shown in FIG. 5A.

FIGS. 5A-5C are schematic diagrams illustrating an exemplary construction of an overmold used in construction of an IMD according to the present invention. FIG. 5A illustrates that IMD 501 comprises a set of modules 510-512, a set of motion restriction elements, such as motion restriction fibers 521. In FIG. 5A, motion restriction fibers 521 are coupled to modules 510 and 511, and are covered at least in part by overmold 522. Overmold 522 typically includes a solid biocompatible material. Overmold 522 may comprise an elastomeric material that is soft and flexible, such as silicone. In addition or in the alternative, overmold 522 may comprise a non-elastomeric material that imparts rigidity to IMD 501. In one embodiment, for example, a non-elastomeric material in overmold 522 acts as a "frame" to hold the modules in a fixed position relative to one another, and does not fully cover the modules. Overmold 522 covers, at least in part, the components and modules within IMD 501 while providing a flexible structure that permits the device 501 to conform to fit each individual patient. Because overmold 522 is typically flexible, IMD 501 may benefit from motion restriction devices such as motion restriction fibers 521, which provide structural integrity to device 501 once implanted into the patient.

Additional details regarding the set of motion restriction devices 521 are described in co-pending and commonly assigned U.S. Patent Application entitled "REDUCING RELATIVE INTER-MODULE MOTION IN A DISTRIBUTED MODULAR IMPLANTABLE MEDICAL DEVICE," assigned U.S. application Ser. No. 10/731/881.

FIG. 5B illustrates that the overmold 522 may include a non-elastomeric, or "hard" component 531 in addition to an elastomeric, or "soft" component 532. In FIG. 5B, the non-elastomeric component 531 is shaped to conform to the shape of at least one of modules 510-512 such that the modules may be restrained from motion by the non-elastomeric components. The non-elastomeric components 531 are typically made of a solid biocompatible material such as polysulfone, and may also be made of metal such as titanium.

The non-elastomeric components 531 are utilized in locations in which motion is to be restricted. Any or all modules may be constrained by one or more hard components 531. Overmold 522, including elastomeric and non-elastomeric components, can be fabricated into a single structure before the modules 510-512 are inserted into the device 501.

Generally, overmold 522 serves a number of functions. For example, overmold 522 incorporates motion restriction elements within the device 501, and attaches to modules and other elements to provide a unified device. In addition, overmold 522 provides a smooth interface surface for the device as it interacts with the patient, and protects electrical connections and feed through wires that connect modules to external leads.

Overmold 522 may also include a durometric specific material to provide desired device qualities such as flexibility and structural integrity. In addition, the material used to construct overmold 522 may possess a thermal conductivity characteristic to either act as a heat sink, or act as an insulator to shield the patient 100 from any excess heat from IMD 501. Because IMD 501 may be constructed from a large number of modules to perform a desired task, the materials selected for used in constructing the overmold 522 may vary as needed by each embodiment.

FIG. 5C illustrates that overmold 522 provides sloped interface 541 between an exemplary module 542 within IMD 501 and the patient's body. In embodiments in which IMD 501 is implanted within tight spaces, such as under the scalp of the patient, sloped interface 541 provides a smooth transition and eases sharp edges that are known to cause possible points of stress for tissue. An angle of interface from the patient's body and the sloped interface 541 can be approximately 135 degrees.

Additional details regarding the overmold 522 are described in co-pending and commonly assigned U.S. Patent Application entitled "OVERMOLD FOR A MODULAR IMPLANTABLE MEDICAL DEVICE," assigned U.S. application Ser. No. 10/730,873.

In the exemplary embodiments depicted in FIGS. 5A-5C, any two modules may be interconnected via one or more coupling modules (not shown in FIGS. 5A-5C). In addition to considerations identified above, the particular coupling modules may depend upon the configuration of the overmold, the configuration of elastomeric and non-elastomeric components; the presence of motion restriction devices, and so on.

Figure 6A:
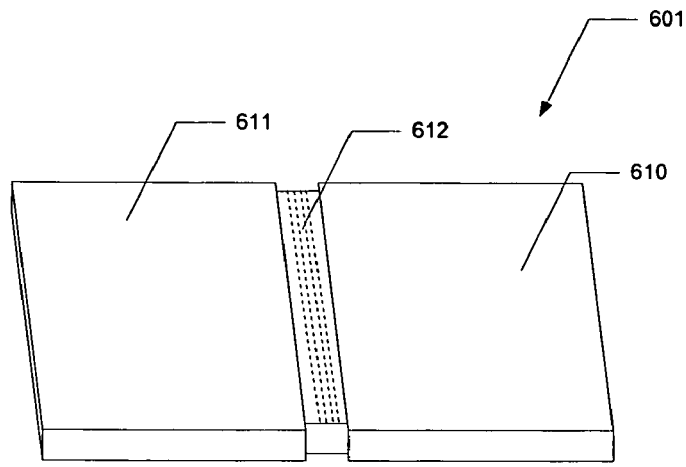
FIGS. 6A-6C are schematic diagrams illustrating distributed modules and a coupling module with a single degree of freedom of motion according to an embodiment of the present invention.
Figure 6B:
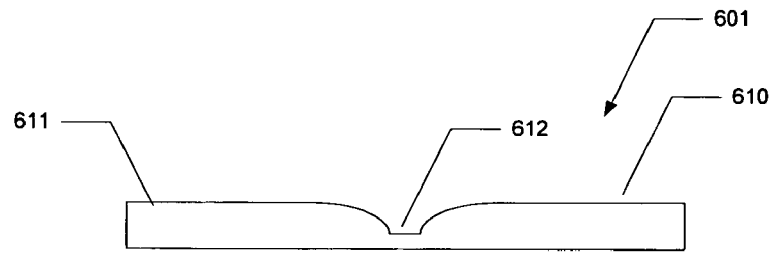
Figure 6C:
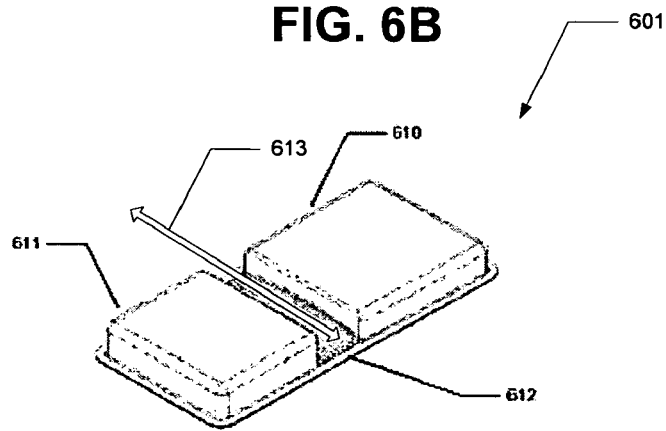

FIGS. 6A-6C are schematic diagrams illustrating two distributed modules 610, 611 having a coupling module 612 according to an embodiment of the present invention. In FIGS. 6A-6C, coupling module 612 provides a single degree of freedom to move. In particular, coupling module 612 limits motion of modules 610, 611 relative to one another to a single axis.

IMD 601 shown in this embodiment is constructed from two individual modules 610-611 that are physically linked using a flexible coupling module 612 that may also be referred to as a "power pipe module." This coupling module possesses a coupling body having a connection end at each connection interface with a module. In a typical implementation, a coupling module 612 interfaces with a module by being coupled to a housing of the module. In each of the three embodiments shown in FIGS. 6A-6C, coupling module 612 constrains translational motion of one module relative to another. In FIGS. 6A-6C, coupling module 612 includes a flexible zone that is bendable.

In FIGS. 6A-6C, coupling module 612 is generally narrower than the dimensions of the modules 610-611. Furthermore, coupling module 612 may be constructed of a more flexible material than the modules, resulting in some freedom of bending. In FIG. 6A, coupling module 612 is depicted as a distinct module coupled to two modules. In FIGS. 6B and 6C, by contrast, coupling module 612 forms part of a unified structure with modules 610 and 611. FIG. 6B illustrates the coupling module 612 as including a narrow zone between two compartments of a common structure, with a module deployed within each of the two compartments 610-611. FIG. 6C shows the coupling module 612 as including a distinctly separate ribbed element that separates the two modules 610-611 and that accommodates some motion of the modules relative to one another.

With the freedom provided by coupling module 612, modules 610-611 may be oriented relative to one another, such that IMD 601 as a whole includes a convex surface. Coupling module 612 may be semi-rigid to permit the IMD 601 to be manipulated into a desired shape and then retain modules 610-611 in a desired orientation. Alternatively, coupling module 612 may flexibly permit modules 610-611 to move freely about an axis of rotation 613.

Coupling module 612 defines at least one lumen or passageway. This lumen (not shown in FIGS. 6A-6C) permits components and elements in one module 610 to be mechanically or electrically coupled to other components and elements in the other module 611. Coupling module 612 provides a structural support element that protects these connections between modules from damage. Coupling module 612 may also include one or more hermetic interfaces between a module and coupling module 612 to environmentally protect the modules 610-611 from contamination. In some embodiments, coupling module 612 is hermetically fixed to at least one of the housings of modules 610-611. In other embodiments of the invention, coupling module 612 may be fixed to one or more modules non-hermetically.

Figure 7A:
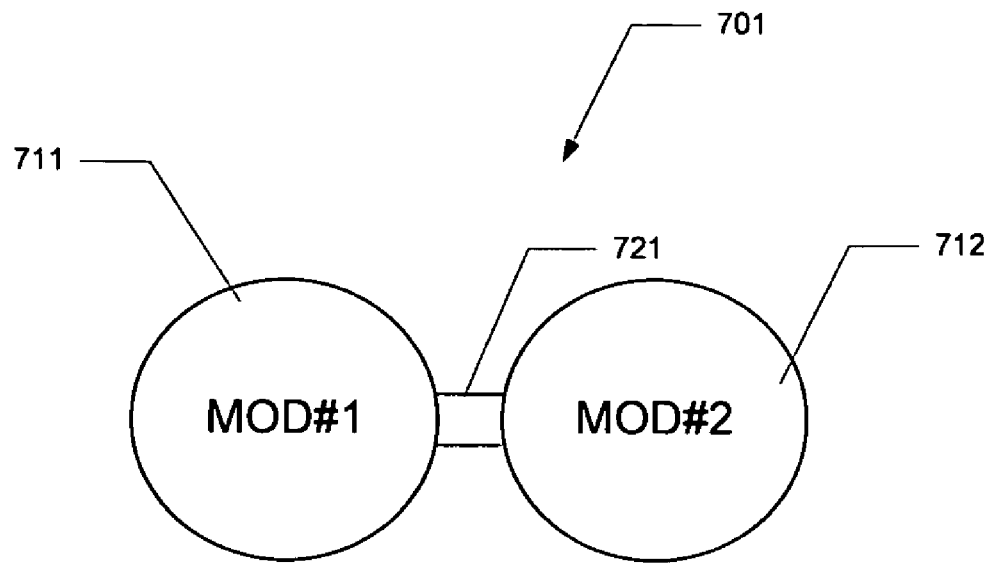
FIGS. 7A-7B are schematic diagrams illustrating distributed modules having a one or more coupling modules with two degrees of freedom of motion according to an embodiment of the present invention.
Figure 7B:
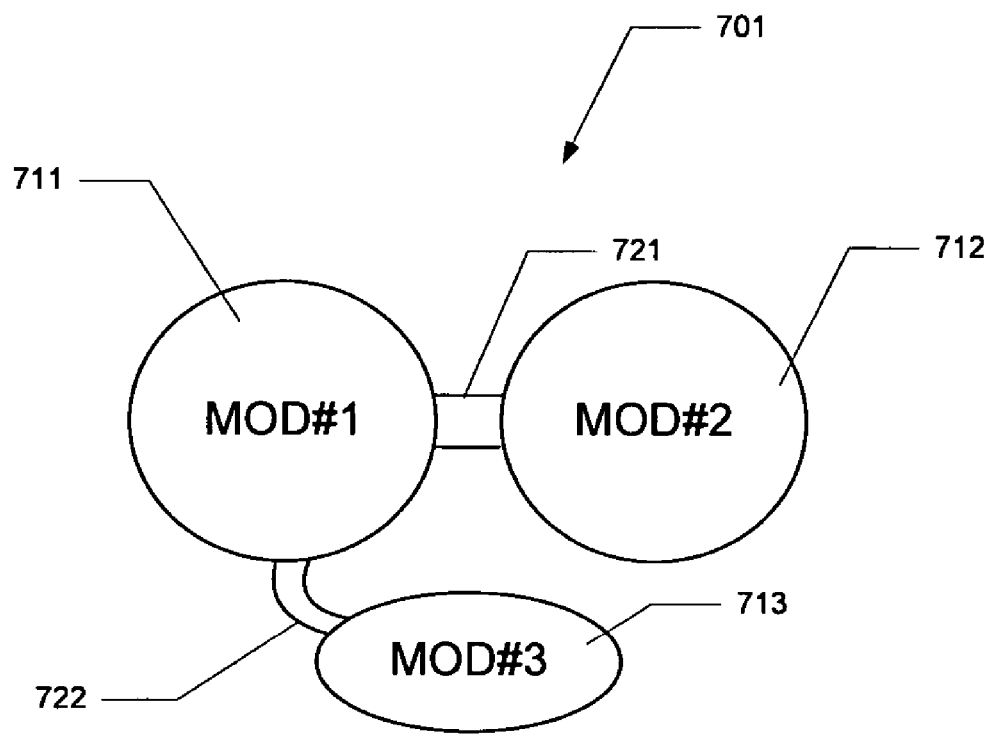

FIGS. 7A-7B are schematic diagrams illustrating two distributed modules having a coupling module with at least two degrees of freedom to move, according to an embodiment of the present invention. IMD 701 shown in these embodiments includes two modules 710-711 that are physically linked using a coupling module 721 that may typically possess two degrees of motion. In each of the three exemplary embodiments shown in FIGS. 7A-7C, a flexible coupling module 721 exists between the two modules 711-712.

In these embodiments, the flexible coupling module 721 may flex about two axis of rotation that correspond to dimensions of the of coupling module 721 that are most narrow. Coupling module 721 may rotate in a pitch and yaw axis, for example, but not in a roll axis.

In FIG. 7B, IMD 701 includes a third module 713 coupled to another module 711 via a second coupling module 722. Coupling module 722, like coupling module 721, may support two axes of motion. As a result, the individual modules 711, 712, 713 may be oriented relative to one another in three dimensions. Coupling module 722, like coupling module 721, may be hermetic or non-hermetic. Coupling modules 721 and 722 may have, but need not have, comparable degrees of flexibility.

Figure 8:
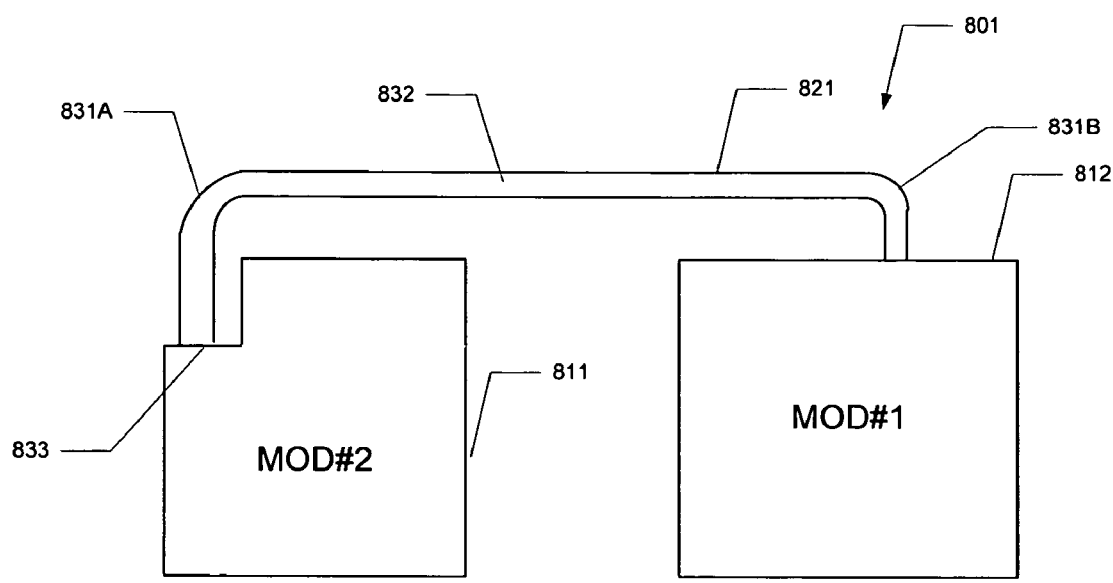
FIG. 8 is schematic diagram illustrating distributed modules having a coupling module with three degrees of freedom of motion according to an embodiment of the present invention.

FIG. 8 is schematic diagram illustrating an IMD 801 having two distributed modules 811, 812 with a coupling module 821 that affords three degrees of freedom to move, according to an embodiment of the present invention. In FIG. 8, modules 811-812 are physically linked with coupling module 821. Coupling module 821 affords some freedom to orient modules 811-812 so that modules 811-812 are not co-planar. Modules 811 and 812, may be moved closer or farther apart by flexing coupling module 821 at bend 831A or bend 831B, or both. Modules 811 and 812, may also be twisted relative to one another by bending or twisting elongated section 832. In the embodiment shown in FIG. 8, module 811 includes a notched connection point 833 that enables an enhanced range of motion.

The degree of motion is a function of the configuration of the coupling module, such its length or the number and placement of bends, and the material from which the coupling module is constructed. In one embodiment, the coupling module is formed of titanium. Other materials, such as silicone, other metals such as stainless steel, or polymers such as polysulfone, may also be used to construct the coupling module. Moreover, a coupling module may be constructed from more than one material. In general, a coupling module should be durable and reliable, and should be subject to bending or twisting without damage.

Figure 9:
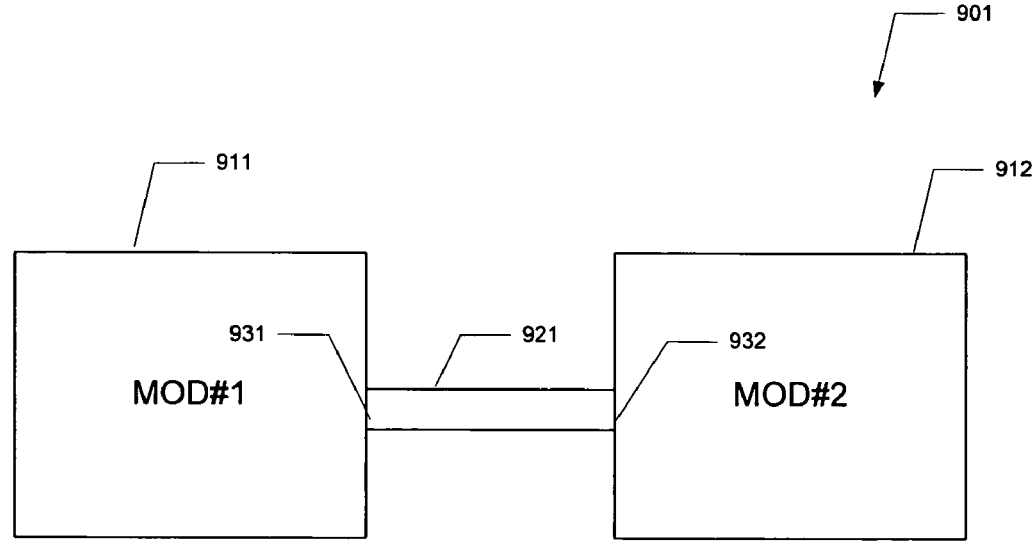
FIG. 9 is schematic diagram illustrating distributed modules having a coupling module having a hermetic and non-hermetic interconnection according to an embodiment of the present invention.

FIG. 9 is schematic diagram illustrating an IMD 901 with two distributed modules 911 and 912 and a coupling module 921 having both a non-hermetic boundary 931 and a hermetic boundary 932. In this embodiment, the boundary between module 911 and coupling module 921 is non-hermetic. In contrast, the boundary between module 912 and coupling module 921 is hermetic. Such an arrangement may make the fabrication of IMD 901 simpler as it eliminates a hermetic interconnection boundary that imposes cost, complexity and size limitations. In some circumstances, hermetic sealing of module components is unnecessary.

The nature of the hermetic interfaces above described refer to the interfaces between modules and the coupling modules. As such, the overall device 901 may possess no hermetic interfaces between these modules, and may permit passage of liquid or gaseous material between modules, while the entire structure of IMD 901 remains hermetically sealed from the patient. In another embodiment, one module, such as a non-hermetic battery may be enclosed within a hermetically sealed module that does not permit battery material to pass into a coupling module and any other modules. In this embodiment, the entire device 901 may also be hermetically sealed from the patient. In a third embodiment, the various interfaces between all modules and a particular coupling module may possess hermetic interfaces while the coupling module itself is not hermetically sealed to the patient. As such, a coupling module containing an AC power connection between modules may not require a hermetically sealed coupling module with respect to the patient. All of these variations are contemplated to be within the spirit and scope of the present invention as recited within the attached claims.

In addition, the lumen defined by coupling module 921 need not be empty or filled with air. In some embodiments, coupling module 921 may be back filled with fluids and other materials. Such materials may, for example, offer some isolation of components disposed in the coupling module, or may insulate, or may dissipate heat, or may absorb gases that may be emitted by a battery in a power supply module.

FIGS. 10A-10I are schematic diagrams illustrating exemplary coupling module shapes and configurations according to embodiments of the present invention. Coupling module 1001 provides a protected interconnection volume between two modules within a modular IMD. The particular shape for the coupling module 1001 may be affected by the nature of the interconnection between the two modules, the orientation of the modules, the size of the lumen, the desired degree of flexibility, and the like. One generally desirable characteristic of the coupling module is that it be flexible enough to accommodate some motion of the modules relative to one another without becoming damaged. Some embodiments of coupling module 1001 may also provide structural protection and support for the module interconnection.

Figure 10A:
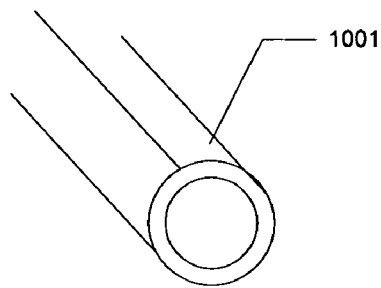
Figure 10B:
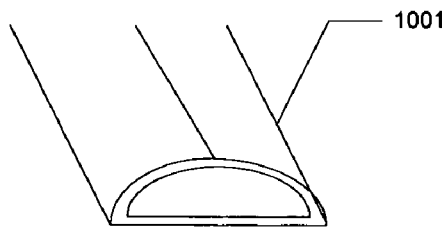
Figure 10C:
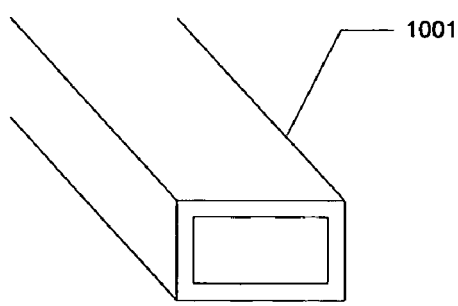

FIGS. 10A-10C illustrate a coupling module 1001 having a single lumen connecting two modules. FIG. 10A illustrates a round or circular lumen. FIG. 10B illustrates a semi-circular lumen. FIG. 10C illustrates a rectangular lumen. The invention is not limited to a lumen having any particular cross-section, and includes coupling modules having cross-sections not specifically shown herein.

Figure 10D:
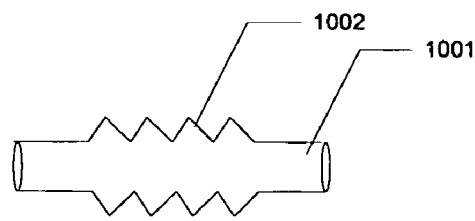

FIG. 10D illustrates a coupling module 1001 that possesses a bellows section 1002 as part of its structure. Bellows 1002 enhances the flexibility of coupling module 1001. In particular, the embodiment of coupling module 1001 depicted in FIG. 10D illustrates a coupling module that includes variations in the cross-sectional diameter that accommodate motion along one or more axes of motion. The bellows configuration in FIG. 10D is illustrative, and the invention includes embodiments that comprise corrugations, convolutions, or other variations in cross-sectional shape that impart degrees of freedom of movement.

FIG. 10E illustrates that a coupling module 1001 of any configuration discussed herein may include multiple lumens. The lumens may provide independent interconnection paths that are separate from each other. These multiple lumens permit the coupling module to provide connections that are isolated from one other. In FIG. 10E, lumens 1003A and 1003B are side-by-side. FIG. 10F illustrates a coupling module 1001 having coaxial lumens. In FIG. 10F, the lumens include an inner conductor 1004A and an outer conductor 1004B separated from inner conductor 1004A by a dielectric 1005, such that coupling module is similar to a coaxial cable. In some embodiments, the lumens of a coaxial coupling module need not include conductors or dielectrics. The invention encompasses embodiments in which lumens are configured in a concentric fashion.

Figure 10I:
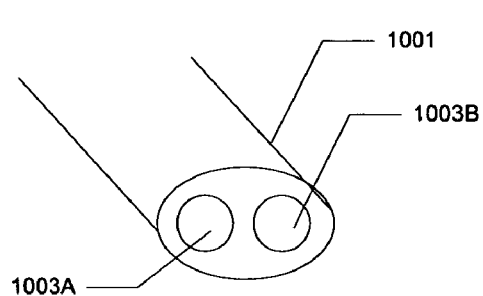
Figure 10I:
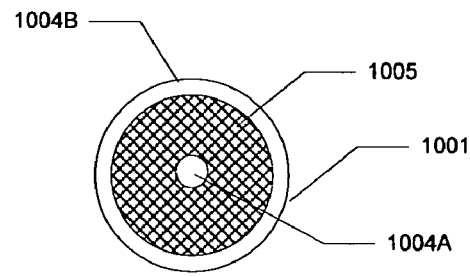
Figure 10I:
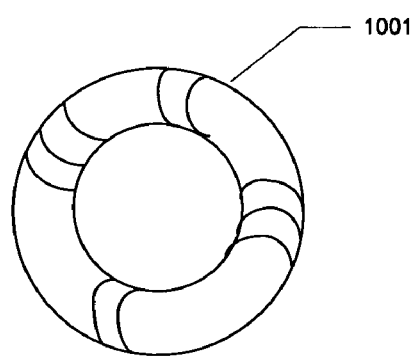
Figure 10I:
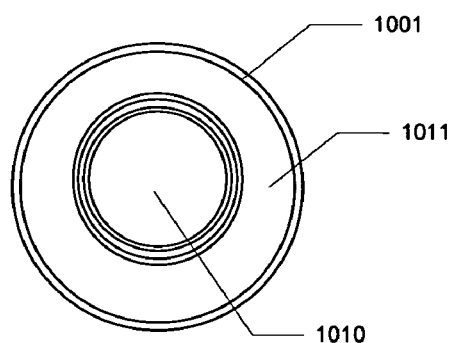
Figure 10I:
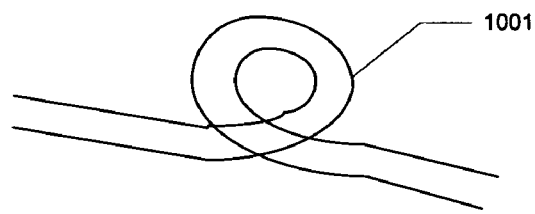

FIG. 10G illustrates a coupling module 1001 that is a ring-like structure having a plurality of separate conduit segments around the ring. FIG. 10H illustrates another concentric arrangement for conduits in which an inner conduit 1010 is separated from an outer conduit 1011. Finally, FIG. 10I illustrates that a coupling module may be arranged to include a helix-like structure. A helix-like structure may, for example, tend to permit more motion along some axes and less motion along others.

In some embodiments of the invention, a coupling module may include a combination of features shown in FIGS. 10A-10I. For example, a coupling module may include a straight portion and a helical portion, or multiple lumens and a bellows section. The invention encompasses all of these combinations.

FIGS. 11A-11M are schematic diagrams illustrating configurations of multiple modules having a coupling module interconnecting two modules according to embodiments of the present invention. FIGS. 11A-11M illustrate various arrangements of interconnected modules used to construct an IMD. These arrangements illustrate some of arrangements for in-line and triangular configurations of the modules. These arrangements illustrate use straight and helix-like arrangements of the coupling modules. Finally, these arrangements illustrate interconnection of modules from adjacent module surfaces or sides as well as interconnection of non-adjacent sides of modules.

Figure 11A:
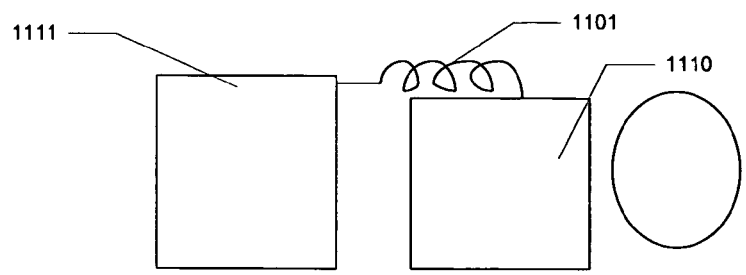
FIGS. 11A-11M are schematic diagrams illustrating configurations of multiple modules and a coupling module according to embodiments of the present invention.
Figure 11B:
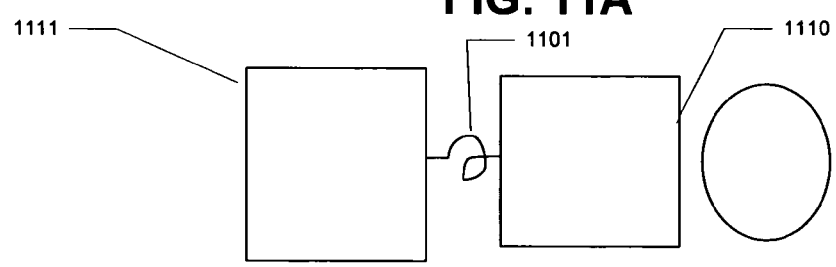
Figure 11C:
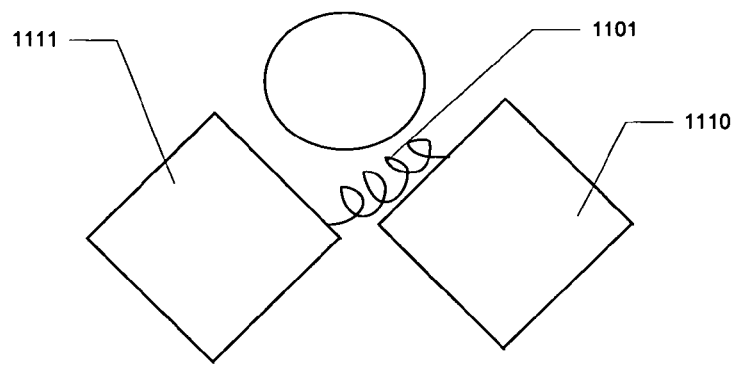
Figure 11D:
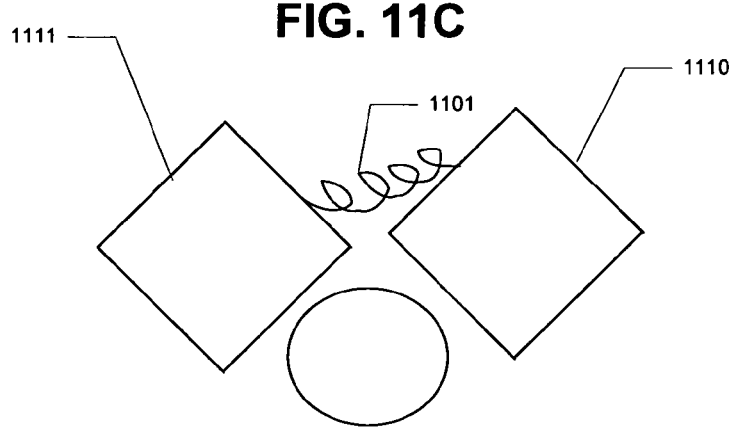
Figure 11E:
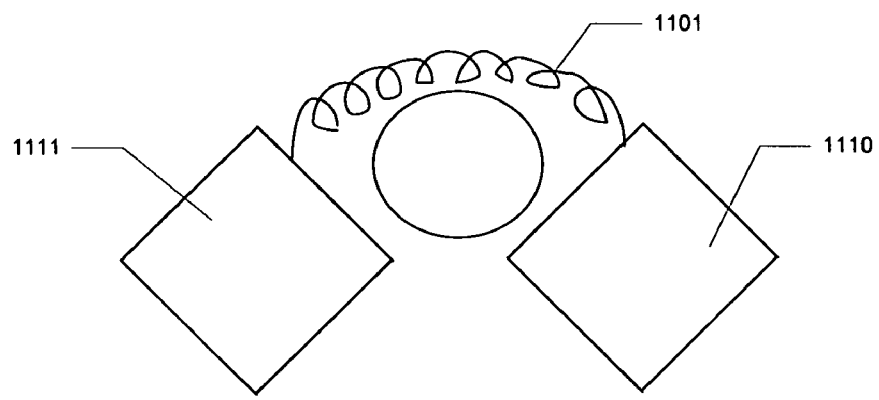
Figure 11F:
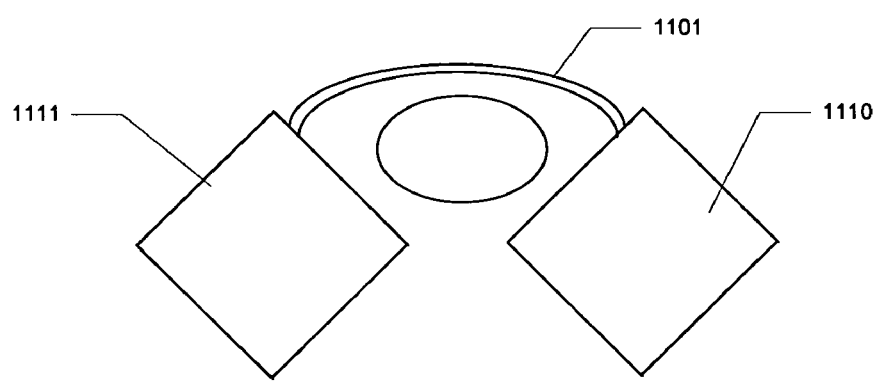
Figure 11G:
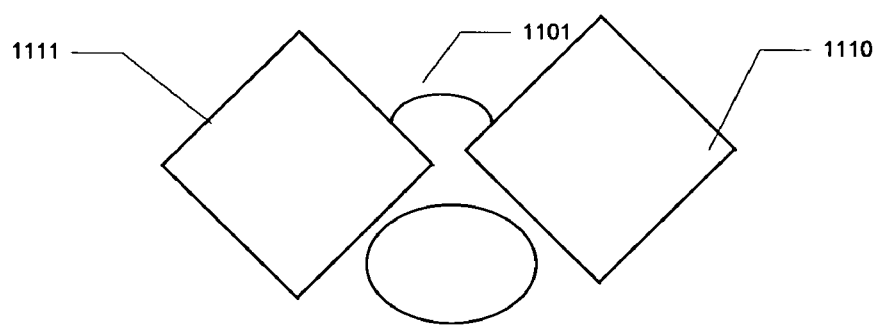
Figure 11H:
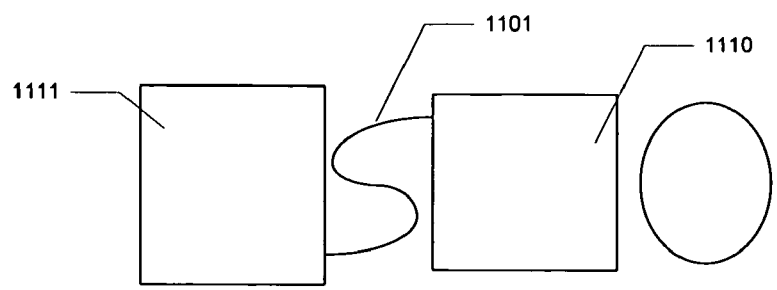
Figure 11I:
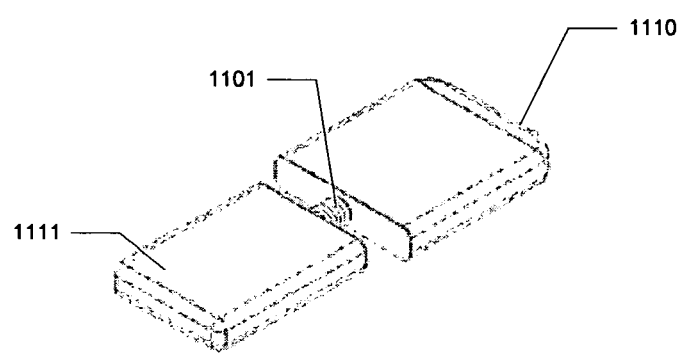
Figure 11J:
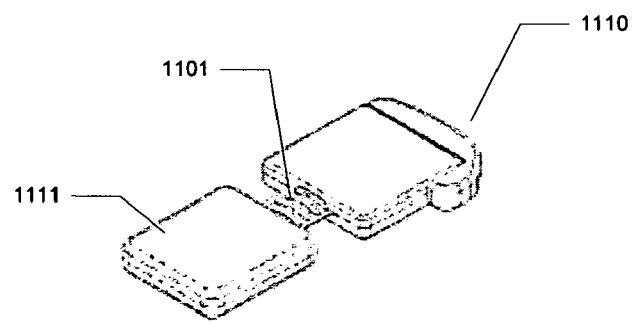
Figure 11K:
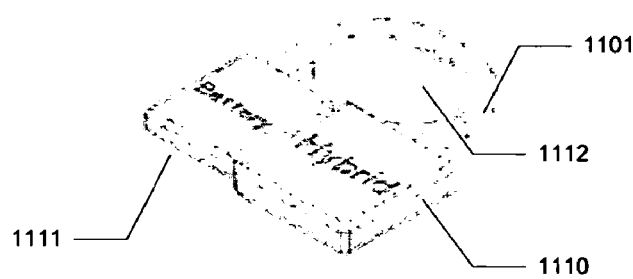
Figure 11L:
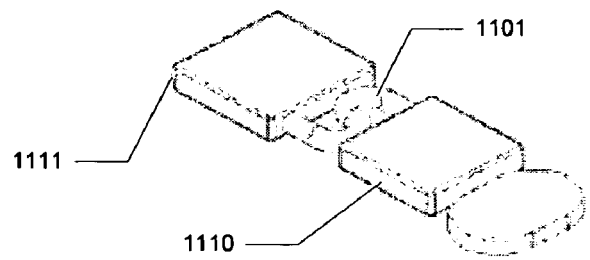
Figure 11M:
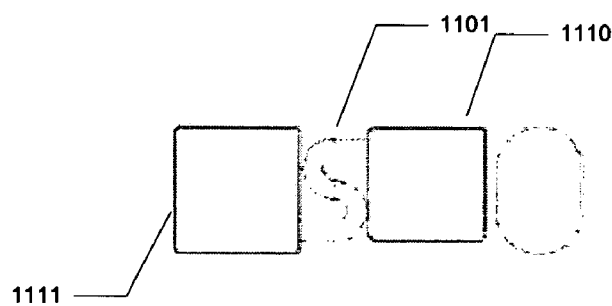

Combination of various features gives rise to the exemplary arrangements shown in FIGS. 11A-11H. In particular, coupling module 1101 may include a combination of straight, curved or helical sections when coupling module 1110 to module 1111. FIGS. 11I and 11J illustrate more rigid coupling module 1101 arrangements between adjacent sides of two modules 1110-1111. FIG. 11K illustrates that a coupling module 1101 may connect two modules 1110-1111 by bending around a third module 1112. Finally, FIGS. 11L-11M illustrate the interconnection of two modules 1110-1111 using an S-shaped coupling module 1101. Embodiments in FIGS. 11L-11M include any arrangement and shape for a connection body used to construct a coupling module possessing at least one non-linear bend.

The invention is not limited to the particular coupling module configurations shown herein. The possible arrangements of IMD modules and coupling modules is virtually unlimited.

Figure 12A:
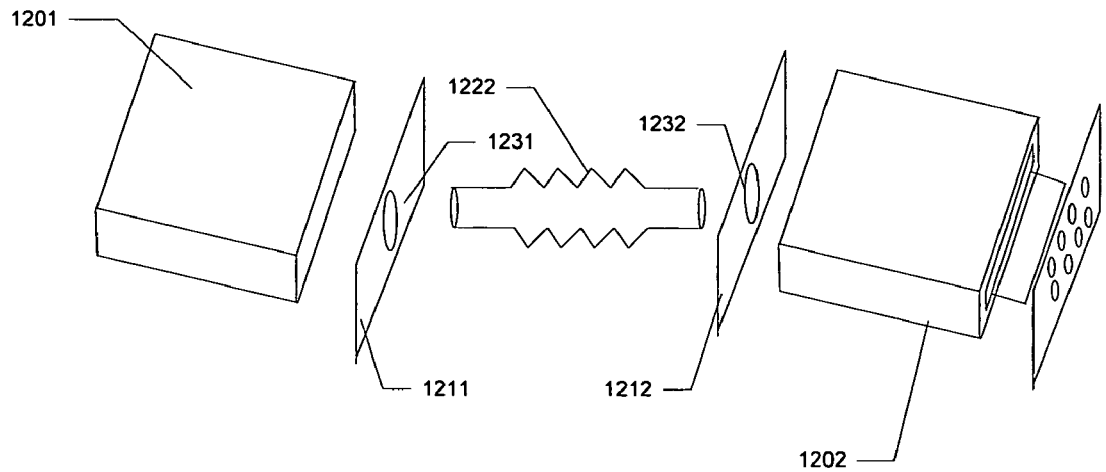
FIGS. 12A-12C are schematic diagrams illustrating module interfaces with a coupling module according to an embodiment of the present invention.
Figure 12B:
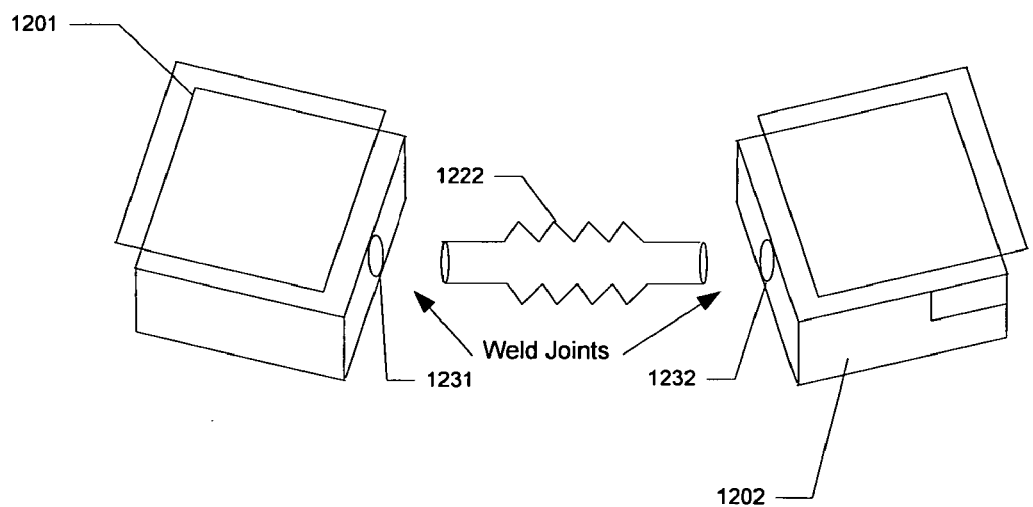
Figure 12C:

FIGS. 12A-12C are schematic diagrams illustrating module interfaces with a coupling module according to an embodiment of the present invention. FIGS. 12A-12B illustrate construction of two distributed modules from case components 1201-1202, module end caps 1211-1212, and a flexible interconnection coupling module 1222. The module end caps 1211-1212, and a flexible interconnection coupling module 1222 are mechanically coupled using weld joints 1231-1232. The module end caps 1211-1212 may be coupled to case components 1201-1202 with welds or braze joints. As is discussed above, these connections mat be either hermetic, as shown, or non-hermetic. FIG. 12C illustrates a completed module end cap and coupling module assembly 1241 that may be further coupled to two modules (not shown) to construct a modular IMD.

Figure 13:
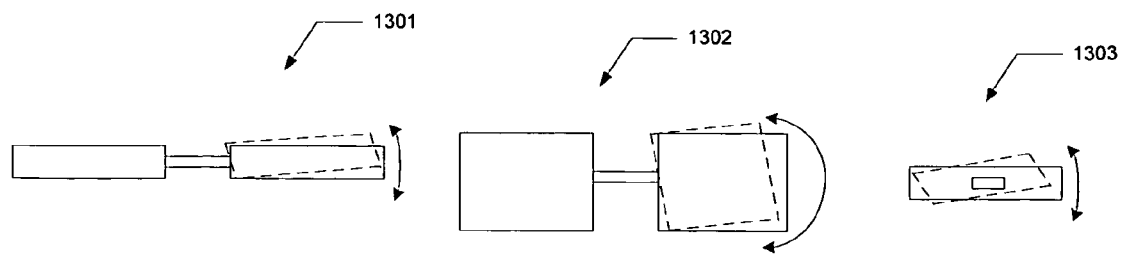
FIG. 13 is a schematic diagram illustrating the axes of motion present in a multi-module implantable medical device.

FIG. 13 is a schematic diagram illustrating the degrees of motion present in a multi-module IMD. For any two modules within a modular medical device, motion between the two devices may be defined in terms of pitch motion 1301 (shown in side view), yaw motion 1302 (shown in top view), and roll motion 1303 (shown in end view). For the set of motion restriction elements (not shown) discussed above, all three degrees of motion may be limited to prevent mechanical failures of interconnections between the modules during use of an IMD.

Figure 14A:
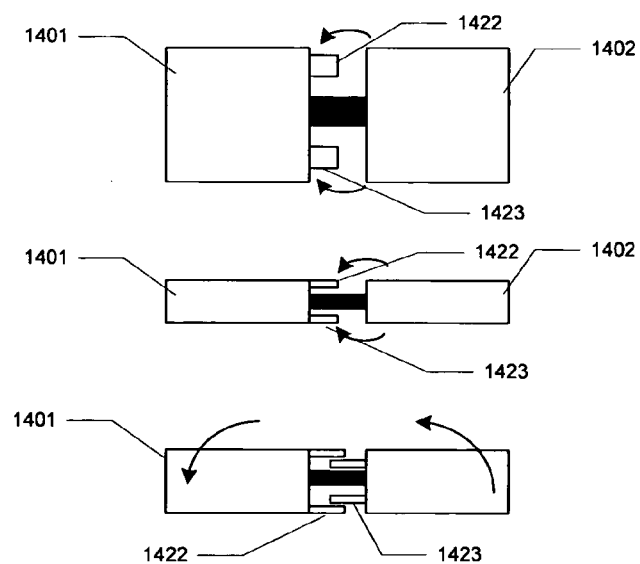
FIGS. 14A-14C are a schematic diagrams illustrating motion restriction of a multi-module implantable medical device.
Figure 14B:
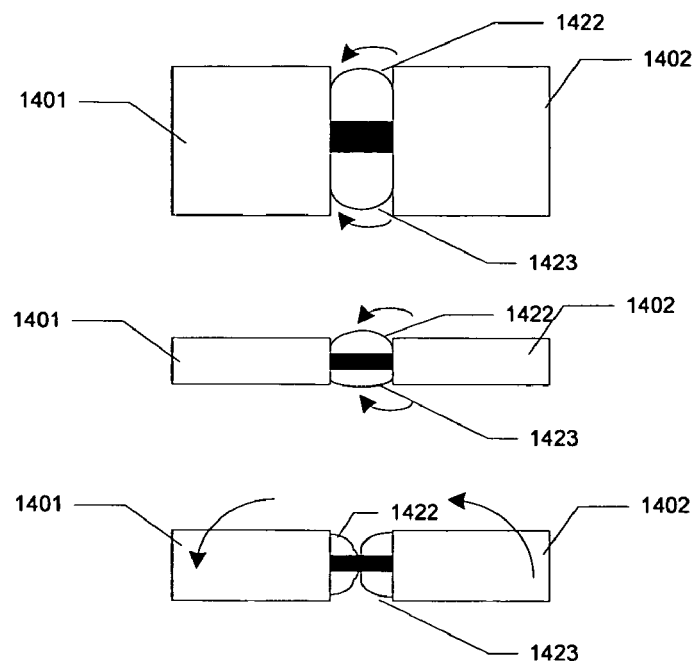
Figure 14C:
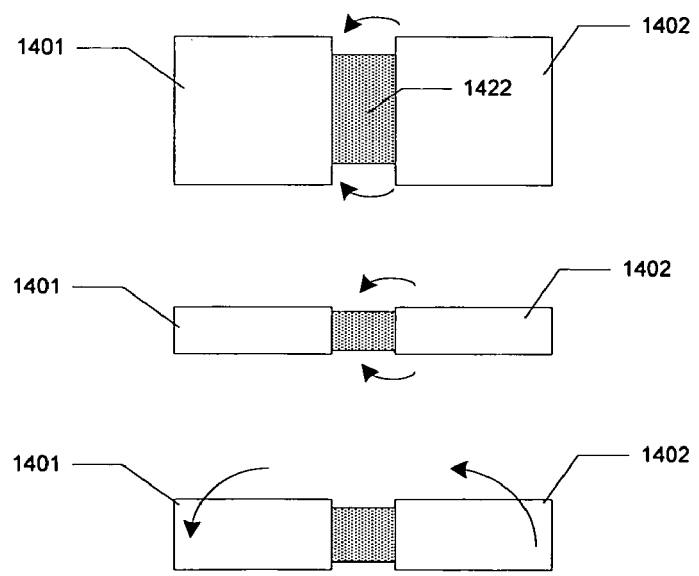

FIGS. 14A-14C are a schematic diagrams illustrating motion restriction within various degrees of motion within a multi-module IMD. For any two modules 1401-1402 within an IMD, motion restriction elements 1422-1423 may be employed to constrain the relative orientation of modules 1401-1402. Motion restriction elements 1422-1423 may be sufficient to restrain motion, thereby reducing the risk of potentially damaging stress upon a coupling module. In some embodiments, motion restriction elements 1422-1423 are typically successful in adequately restricting motion in one or two degrees of motion. These degrees of motion are typically along an axis in which the elements 1422-1423 possess most of their strength. For example, motion restriction elements 1422-1423 may constrain motion along a yaw and pitch axis but provide little or no constraint along the roll axis.

FIG. 14A illustrates an embodiment in which the motion restriction elements 1422-1423 include one or more physical members that physically interact to restrain motion. FIG. 14B illustrates an embodiment in which the motion restriction elements 1422-1423 include one or more wire loops that oppose each other to restrain motion. FIG. 14C illustrates an embodiment in which the motion restriction elements 1422-1423 include a fabric that physically restrains motion. In alternate embodiments, motion restriction elements may be used to constrain motion along one or all axes.

Additional details regarding the set of motion restriction elements 1422-1423 described in co-pending and commonly assigned U.S. Patent Application entitled "REDUCING RELATIVE INTER-MODULE MOTION IN A DISTRIBUTED MODULAR IMPLANTABLE MEDICAL DEVICE," assigned U.S. application Ser. No. 10/731,881.

Figure 15A:
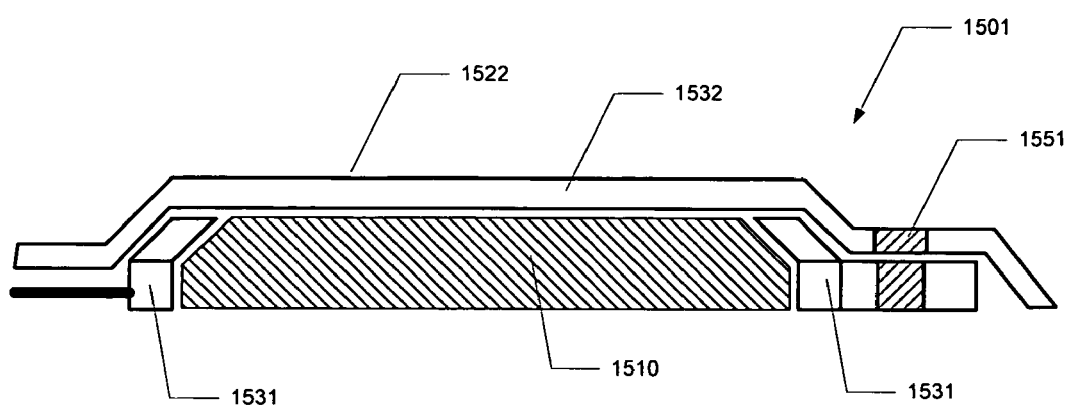
FIGS. 15A-15B are schematic diagrams illustrating the interaction of components of an implantable medical device that are part of an overmold according to the present invention.
Figure 15B:
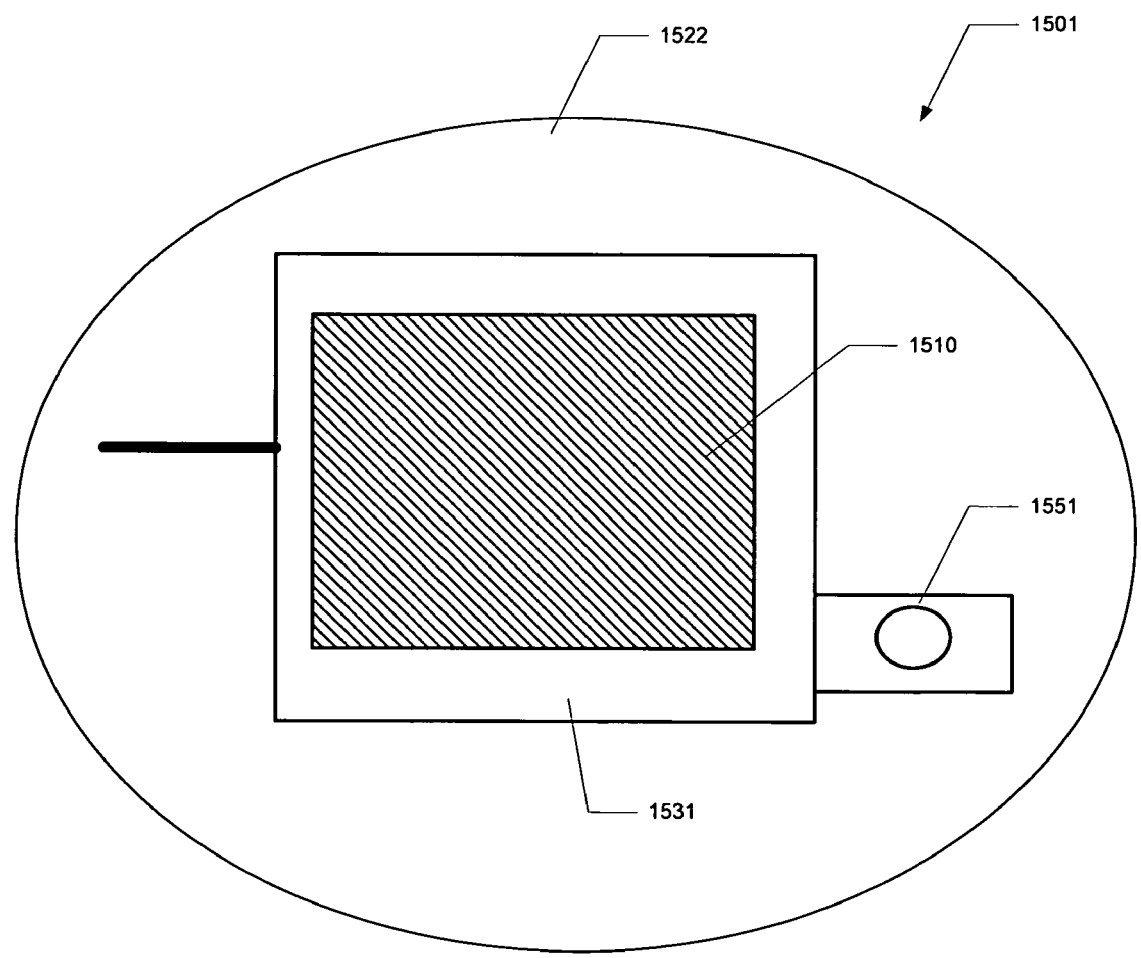

FIGS. 15A-15B are schematic diagrams illustrating an exemplary interaction of components of an IMD that are part of an overmold 1522, which includes one or more soft or elastomeric components 1532 and one or more hard or non-elastomeric components 1531, which interface with a control module 1510. Non-elastomeric component 1531 may be shaped to mate with the module 1510 to provide motion restriction for the module. Non-elastomeric component 1531 may be mechanically connected to other modules using a motion restriction element (not shown). The overmold 1522 covers all of these components in this embodiment. A through hole 1551 may be located through the through the non-elastomeric component 1531 and elastomeric component 1532 to provide an attachment point for the device 1501. In some embodiments, IMD 1501 may be anchored in place using bone screws or other anchoring devices. Through holes 1551 permit IMD 1501 to be mechanically anchored to the patient once the device 1501 is positioned at a desired location. In the embodiment shown in FIG. 15A, a bone screw inserted into through hole 1551 would seat against non-elastomeric component 1531, but the invention encompasses embodiments in which a bone screw would seat against another component, such as control module 1510.

FIG. 15B illustrates a top view of the device 1501 having elastomeric component 1532 of overmold 822 covering the non-elastomeric components 1531 that frame control module 1510. The through hole 1551 used as an attachment point is shown as part of non-elastomeric component 1531 that is covered by elastomeric component 1532. The shape of non-elastomeric component 1531 and control module 1510 are shown as being rectangular in this embodiment. However, one skilled in the art will recognize that any shape for non-elastomeric component 1531 and control module 1510 may be used without deviating from the spirit and scope of the present invention.

In addition, overmold 1522 is shown in FIGS. 15A and 15B as substantially or completely encapsulating module 1510. However, overmold 1522 may also merely surround the module 1510 but not cover the top of the module that is surrounded by the hard component 1531. Such an arrangement may result in a smaller profile of the overall IMD.

A coupling module (not shown) passes around and through many of the elements of the overmold. This coupling module may be, but need not be, constrained within overmold 1522. In general, the coupling module may be expected to flex during implantation and use. In some embodiments of the invention, the coupling module may be routed in a channel (not shown) within the overmold.

Additional details regarding the overmold are described in co-pending and commonly assigned U.S. Patent Application entitled "OVERMOLD FOR A MODULAR IMPLANTABLE MEDICAL DEVICE," assigned U.S. application Ser. No. 10/730,873.

Figure 16A:
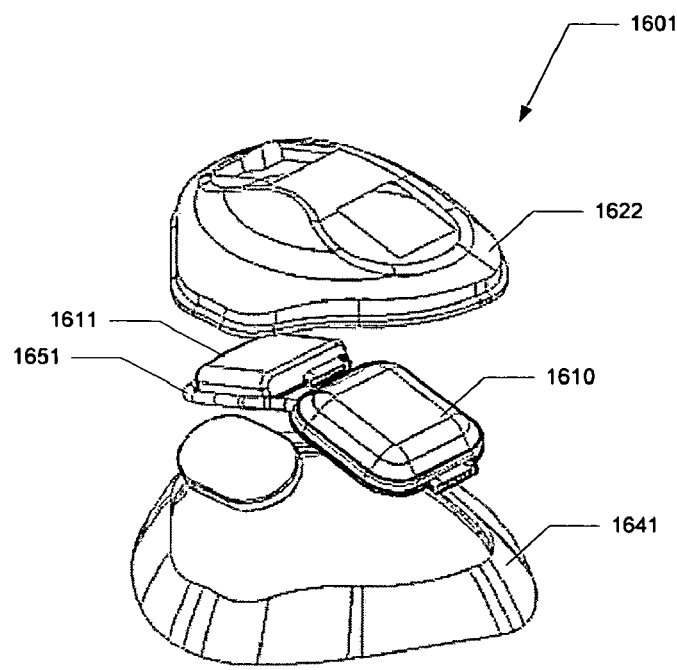
FIGS. 16A-16B are a perspective diagrams illustrating a multi-module implantable medical device having an triangular module arrangement and a coupling module according to the present invention.
Figure 16B:
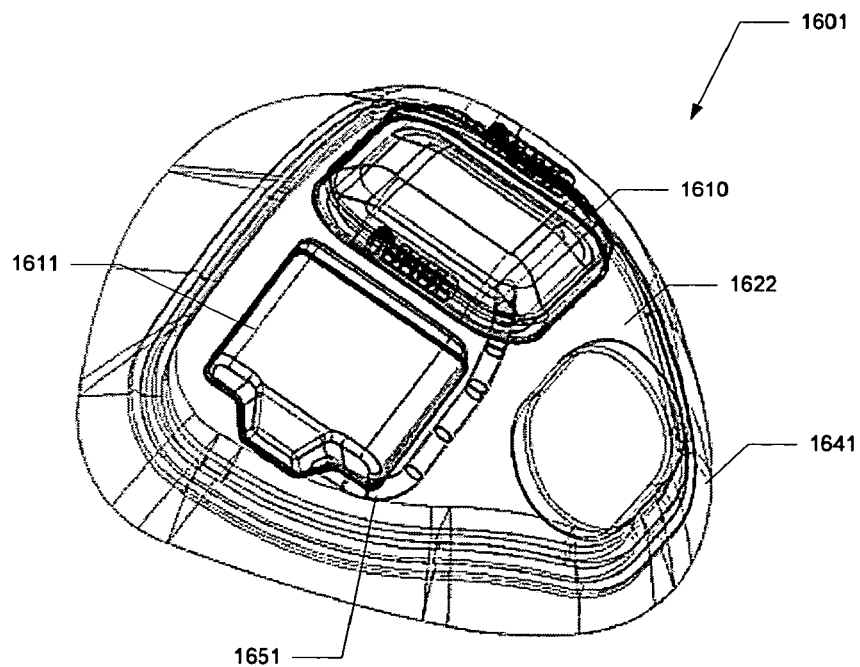

FIGS. 16A-16B are a schematic diagrams illustrating a multi-module IMD 1601 having a triangular module arrangement according to the present invention. FIG. 16A illustrates an exploded view of IMD 1601. FIG. 16B illustrates a perspective view of IMD 1601. In this embodiment, another triangular arrangement of modules is shown with an overmold 1622 covering or at least partially encapsulating the modules. In this embodiment, overmold 1622 comprises a distinct slope interface 1641 that surrounds the periphery of IMD 1601. In this embodiment, slope interface 1641 is shown as a separate physical structure, such as a flexible band or ring. A coupling module 1651 is shown connecting two modules 1610-1611 without being restrained by the overmold 1622.

While the above embodiments of the present invention describe a coupling module of a modular IMD, one skilled in the art will recognize that the use of a module structure are merely example embodiments of the present invention. It is to be understood that other embodiments may be utilized and operational changes may be made without departing from the scope of the present invention as recited in the attached claims. Although the dimensions of different embodiments of coupling modules may vary, the dimensions of typical coupling modules are such that the coupling module need not be responsible for the thickest portion of the IMD.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a coupling module of a modular IMD.

The invention claimed is:

1. An implantable medical device comprising:
   at least two modules, each of the modules comprising a respective one of at least two housings, wherein each housing in the at least two housings provides a respective space within the housing, each respective space containing one or more components of the implantable medical device;
   a coupling module coupled to each of the modules, the coupling module defining at least one lumen between the housings, the at least one lumen connecting the spaces within at least two of the housings; and
   an overmold that at least partially encapsulates each of the housings and the coupling module,
   wherein the coupling module permits motion of the two modules along at least one axis of motion.

2. The implantable medical device of claim 1, wherein the coupling module permits motion of the two modules along at least two axes of motion.

3. The implantable medical device of claim 1, wherein the coupling module defines at least two lumens.

4. The implantable medical device of claim 1, wherein at least one of the two modules comprises a control module containing electronic components.

5. The implantable medical device of claim 1, wherein the implantable medical device has a maximum thickness of between approximately 4 millimeters and approximately 8 millimeters.

6. The device of claim 1, further comprising a conductor passing through the lumen that electrically couples the first and second modules.

7. The device of claim 1, wherein the components include a battery, a telemetry module, and a processor.

8. An implantable medical device comprising:
a first module comprising a first housing wherein the first housing provides a first space within the first housing, wherein the first space contains control electronics;
a second module comprising a second housing, wherein the second housing provides a second space within the second housing, wherein the second space containing one or more components of the implantable medical device; and
a coupling module fixedly coupled to the first and second housings,
wherein the coupling module is hermetically fixed to the first and second housings, wherein the coupling module is made of a metal that defines at least one lumen between the first and second housings, the at least one lumen connecting the first space with the second space, and wherein the coupling module permits motion of the first housing relative to the second housing along at least one axis of motion.

9. The device of claim 8, wherein the coupling module permits motion of the multiple modules along at least two axes of motion.

10. The device of claim 8, wherein the coupling module defines at least two lumens.

11. The device of claim 10, wherein the lumens comprise co-axial lumens.

12. The device of claim 8, wherein the coupling module defines one of a circular cross-sectional shape, a semi-circular cross-sectional shape and a rectangular cross-sectional shape.

13. The device of claim 8, wherein the coupling module includes a bellows section.

14. The device of claim 8, wherein the coupling module includes at least one of a corrugation, convolution, and a variation in cross-sectional shape.

15. The device of claim 8, wherein the coupling module includes at least a helical portion.

16. The device of claim 8, wherein the metal comprises titanium.

17. The device of claim 8, wherein the coupling module is fixedly coupled to at least one housing with a weld joint.

18. The device of claim 8, further comprising:
a third module; and
a second coupling module fixedly coupled to the third module and to at least one of the first and second housings.

19. The device of claim 8, wherein the second module comprises a battery.

20. The device of claim 8, wherein the coupling module is fixedly coupled to portions of the housings that are adjacent to one other.

21. The device of claim 8, wherein the coupling module comprises at least one bend.

22. The device of claim 8, further comprising a conductor passing through the lumen that electrically couples the first and second modules.

23. The device of claim 8, wherein the components include at least one of:
a battery;
a telemetry module; and
a processor.

24. An implantable medical device comprising:
a first module comprising a first housing, wherein the first housing provides a first space within the first housing, wherein the first space contains control electronics;
a second module comprising a second housing, wherein the second housing provides a second space within the second housing, wherein the second space containing one or more components of the implantable medical device; and
a coupling module fixedly coupled to the first and second housings,
wherein the coupling module is hermetically fixed to the first and second housings and defines at least one lumen between the first and second housings, the at least one lumen connecting the first space with the second space, and wherein the coupling module permits motion of the first housing relative to the second housing along at least one axis of motion.

25. The device of claim 24, further comprising one or more conductors traversing the lumen and connecting components within the first space to components within the second space.

26. The device of claim 24, wherein the components include at least one of:
a battery;
a telemetry module; and
a processor.

* * * * *